US012678405B1

(12) United States Patent
Thomas et al.

(10) Patent No.: US 12,678,405 B1
(45) Date of Patent: Jul. 14, 2026

(54) ORAL LIQUID COMPOSITIONS OF CELECOXIB

(71) Applicant: Codadose Incorporated, Flowery Branch, GA (US)

(72) Inventors: H. Greg Thomas, Carrollton, GA (US); Sara Pennington, Oakwood, GA (US); Roy W. Bryant, Dahlonega, GA (US)

(73) Assignee: Codadose Incorporated, Flowery Branch, GA (US)

( * ) Notice: Subject to any disclaimer, the term of this patent is extended or adjusted under 35 U.S.C. 154(b) by 0 days.

(21) Appl. No.: 19/331,880

(22) Filed: Sep. 17, 2025

Related U.S. Application Data

(60) Provisional application No. 63/853,324, filed on Jul. 29, 2025.

(51) Int. Cl.

| | |
|---|---|
| ***A61K 9/10*** | (2006.01) |
| ***A61K 9/00*** | (2006.01) |
| ***A61K 31/415*** | (2006.01) |
| ***A61K 47/02*** | (2006.01) |
| ***A61K 47/10*** | (2017.01) |
| ***A61K 47/12*** | (2006.01) |
| ***A61K 47/14*** | (2017.01) |
| ***A61K 47/26*** | (2006.01) |
| ***A61K 47/36*** | (2006.01) |

(52) U.S. Cl.
CPC .............. *A61K 9/10* (2013.01); *A61K 9/0053* (2013.01); *A61K 31/415* (2013.01); *A61K 47/02* (2013.01); *A61K 47/10* (2013.01); *A61K 47/12* (2013.01); *A61K 47/14* (2013.01); *A61K 47/26* (2013.01); *A61K 47/36* (2013.01)

(58) Field of Classification Search
CPC ...... A61K 9/10; A61K 9/0053; A61K 31/415; A61K 47/02; A61K 47/10; A61K 47/12; A61K 47/14; A61K 47/26; A61K 47/36
See application file for complete search history.

(56) References Cited

U.S. PATENT DOCUMENTS

2016/0346300 A1 12/2016 Kiel et al.

FOREIGN PATENT DOCUMENTS

WO WO-2022/185338 A1 9/2022

*Primary Examiner* — Quanglong N Truong
(74) *Attorney, Agent, or Firm* — Foley & Lardner LLP

(57) ABSTRACT

Liquid pharmaceutical compositions, including suspensions, of celecoxib are provided herein. Methods of preparing the liquid pharmaceutical compositions and methods of using the compositions to treat diseases or disorders are also provided. Methods of determining the dissolution profile of liquid pharmaceutical compositions containing celecoxib are also provided.

22 Claims, 6 Drawing Sheets

ORAL LIQUID COMPOSITIONS OF CELECOXIB

CROSS-REFERENCE TO RELATED APPLICATIONS

This application claims priority to U.S. Provisional Patent Application No. 63/853,324, filed Jul. 29, 2025, the entire contents of which are incorporated by referenced herein.

FIELD

Described are oral liquid pharmaceutical compositions of celecoxib, methods of making them, and therapeutic methods using them, e.g., in the treatment of one or more conditions such as osteoarthritis, rheumatoid arthritis, juvenile rheumatoid arthritis, ankylosing spondylitis, acute pain, and primary dysmenorrhea.

BACKGROUND

Celecoxib, a diaryl-substituted pyrazole chemically named 4-[5-(4-methylphenyl)-3-(trifluoromethyl)-1H-pyrazol-1-yl]benzenesulfonamide, is represented by the following structural formula:

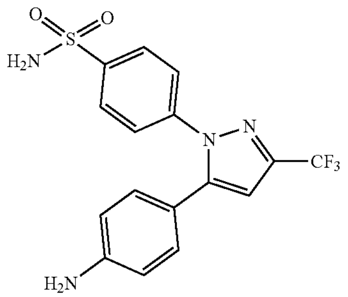 [SMILES: Nc1ccc(-c2cc(C(F)(F)F)nn2-c2ccc(S(N)(=O)=O)cc2)cc1]

Celecoxib is known for therapeutic and prophylactic use based on its activity as a selective inhibitor of the cyclooxygenase-2 (COX-2) enzyme. This enzyme is involved in the in vivo synthesis of prostaglandins. Prostaglandins sensitize afferent nerves and potentiate the action of bradykinin in inducing pain in animal models. Prostaglandins are mediators of inflammation. Since celecoxib is an inhibitor of prostaglandin synthesis, its mode of action may be due to a decrease of prostaglandin in peripheral tissue.

Celecoxib formulated in a solid oral dosage form (oral capsules) is approved in U.S. under the brand name CELEBREX® for the treatment of osteoarthritis, rheumatoid arthritis, juvenile rheumatoid arthritis, ankylosing spondylitis, acute pain, chronic pain, and primary dysmenorrhea. It is available in strengths of 50 mg, 100 mg, 200 mg and 400 mg. The CELEBREX® capsule formulation includes celecoxib, croscarmellose sodium, edible inks, lactose monohydrate, magnesium stearate, povidone, and sodium lauryl sulfate.

Oral liquid dosage forms may be preferred for children and adults who have difficulty swallowing solid oral dosage form. However, celecoxib's poor water solubility and wettability has hampered development of a liquid formulation. Experimental aqueous formulations of celecoxib in suspension form have been reported, however, celecoxib particles are known to aggregate, rendering the formulations unstable.

US 2016/0346300 describes liquid pharmaceutical preparations containing celecoxib, propylene glycol, glycerin, xanthan gum, and at least 50% water. US 2016/0346300 describes that it is undesirable to add magnesium aluminum silicate to large batches to facilitate pH adjustment and processing, and that omission of magnesium aluminum silicate did not have any adverse effect on the final product properties.

There remains a need for liquid formulations of celecoxib that are stable and suitable for oral administration.

SUMMARY

In one aspect, the present disclosure provides liquid pharmaceutical compositions comprising celecoxib, suspending agents comprising xanthan gum and from 0.05% w/v to 2% w/v of a synthetic magnesium aluminometasilicate, and a liquid carrier.

In a second aspect, the present disclosure provides a method of preparing a liquid pharmaceutical composition comprising dispersing celecoxib and suspending agents comprising xanthan gum and a synthetic magnesium aluminometasilicate in a wetting agent to obtain a dispersion, adding the dispersion to a mixture comprising water and at least one water-soluble excipient and mixing to obtain the composition.

In a third aspect, the present disclosure provides methods of administering celecoxib, comprising orally administering to a subject a liquid pharmaceutical composition as described herein.

In a fourth aspect, the present disclosure provides methods of treating a disease or disorder in a subject in need thereof, comprising orally administering to the subject a therapeutically effective amount of a liquid pharmaceutical composition as described herein, optionally wherein the disease or disorder is selected from osteoarthritis, rheumatoid arthritis, juvenile rheumatoid arthritis, ankylosing spondylitis, acute pain, and primary dysmenorrhea.

In a fifth aspect, the present disclosure provides methods for determining the dissolution profile of a liquid pharmaceutical composition comprising celecoxib, comprising:

(a) providing a first vessel comprising a dissolution medium comprising, e.g., 0.04M sodium phosphate tribasic and 0.5% w/v sodium dodecyl sulfate (SDS) having a pH of 11.1 wherein the dissolution medium is at a temperature of 37° C. and optionally is agitated;

(b) adding the liquid pharmaceutical composition to the first vessel and agitating;

(c) obtaining samples from the first vessel at three or more time points from 5 minutes to 90 minutes after adding the liquid pharmaceutical composition to the first vessel; and (d) determining a quantity of dissolved celecoxib in each sample.

BRIEF DESCRIPTION OF THE DRAWINGS

These and other features, aspects, and advantages of the present disclosure will become better understood with regard to the following description and accompanying drawings, where.

DETAILED DESCRIPTION

Figure 1:
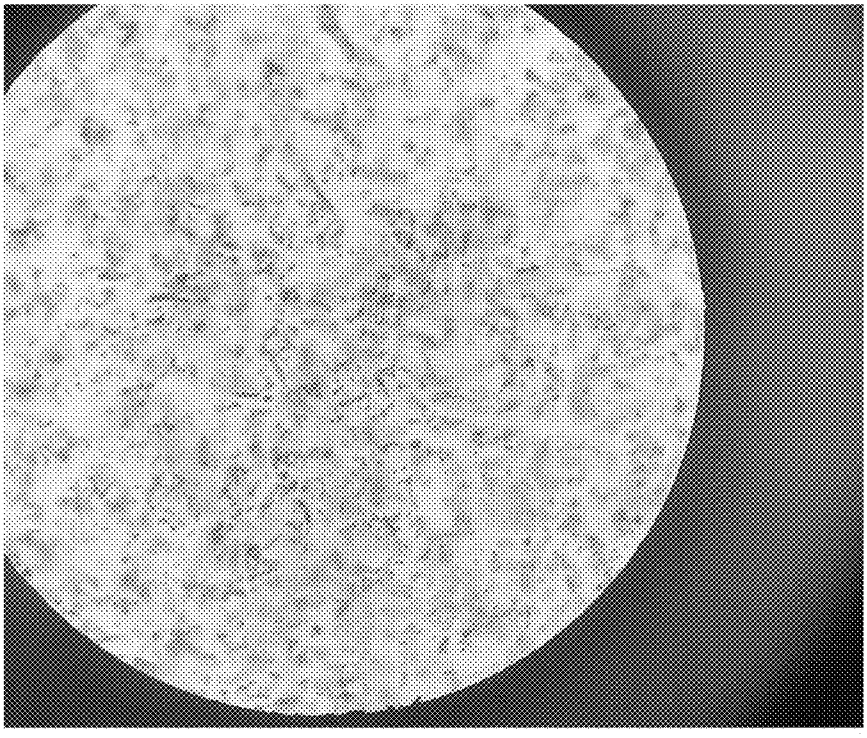
FIG. 1 shows a microscopic image (200×) of an exemplary oral celecoxib suspension formulation of the present disclosure prepared as described in Example 2.

Described herein are oral liquid pharmaceutical compositions of celecoxib, methods of making them, and therapeutic methods using them, e.g., in the treatment of one or more conditions such as osteoarthritis, rheumatoid arthritis, juvenile rheumatoid arthritis, ankylosing spondylitis, acute pain, and primary dysmenorrhea. As described in more detail below, the present inventors determined that formulating celecoxib in a liquid formulation comprising synthetic magnesium aluminometasilicate and xanthan gum as described herein provides a liquid pharmaceutical composition that exhibits advantageous physicochemical properties, including good physical stability (e.g., stability against aggregation and pH changes) and a suitable dissolution profile. In specific embodiments, the described compositions exhibit bioequivalence to CELEBREX® (Celecoxib) capsules (200 mg) (see Example 3).

1. Definitions

In general, terms used herein are intended as "open" terms (e.g., the term "including" should be interpreted as "including but not limited to," the term "having" should be interpreted as "having at least," the term "includes" should be interpreted as "includes but is not limited to," etc.). As such, indefinite articles such as "a," "an," and "the" should be interpreted as singular or plural (e.g., referring one or more), unless the context plainly dictates otherwise. Moreover, the use of introductory phrases such as "at least one" and "one or more" in some instances should not be understood to indicate that the use of "a" or "an" or "the" in other instances is meant to refer to the singular (e.g., only one). Further, if a specific number of features, elements, steps (etc.) is intended, such a number will be explicitly stated.

As used herein, phrases such as "at least one of A, B, and C, etc." should be interpreted as referring to one or more of the listed options (e.g., "a system having at least one of A, B, and C" would include but not be limited to systems that have A alone, B alone, C alone, A and B together, A and C together, B and C together, and/or A, B, and C together, etc.).

In addition, where features or aspects of the disclosure are described in terms of Markush groups, the disclosure should be interpreted as including any individual member of the Markush group and any and all permutations and combinations of subgroups of members of the Markush group.

All ranges disclosed herein should be interpreted as disclosing each individual value within the range (including the endpoints thereof) as well as any and all possible sub-ranges and combinations of sub-ranges thereof, including subranges of equal halves, thirds, quarters, fifths, tenths, etc., unequal subranges, and nested ranges, such as nested ranges centered around a midpoint of a range. Likewise, language such as "up to," "at least," "greater than,' "less than," and the like may be interpreted as open-ended ranges which include a disclosure of sub-ranges as discussed above.

As used herein, "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, "bioequivalence" or "bioequivalent" refers a Test Product (T) that has Test Product to Reference Product (R) ratios of the geometric least squares means for ln-transformed pharmacokinetic parameters $AUC_{0-t}$ and $AUC_{0-inf}$ and their 90% confidence intervals within 80.00%-125.00% of R. Bioequivalence is determined from in vivo human studies in a population.

As used herein, the term "particle" refers to drug substance particles (API alone or in combination with excipients), whether the particles exist alone or aggregated. Particle size distribution can be measured by laser light scattering techniques such as Malvern particle size analyzer. The D10 value of a particle size distribution describes the particle size at which 10% by volume of the particles have a smaller particle size than the particle size corresponding to the D10 value. The D50 value of a particle size distribution describes the particle size at which 50% by volume of the particles have a smaller particle size than the particles corresponding to the D50 value and 50% by volume of the particles have a larger particle size than the D50 value. The D50 value is also referred to as the "average particle size". The D90 value of a particle size distribution describes the particle size at which 90% by volume of the particles have a smaller particle size than the particle size corresponding to the D90 value.

As used herein, the term "pharmaceutically acceptable excipient" refers to those substances that are well accepted by the industry and regulatory agencies such as those listed in monographs published in compendia such as USP-NF, Food Chemicals Codex, Code of Federal Regulations (CFR), FDA Inactive Ingredients Guide and in 21 CFR parts 182 and 184 that lists substances that are generally regarded as safe (GRAS) food ingredients.

As used herein, the term "subject" refers to an animal. Typically, the animal is a mammal. A subject also refers to, for example, primates (e.g., humans, male or female), cows, sheep, goats, horses, dogs, cats, rabbits, rats, mice, fish, birds, and the like. In certain embodiments, the subject is a primate. In some embodiments, the subject is a human.

As used herein, the term "therapeutically effective amount" refers to an amount of a therapeutic agent (e.g., celecoxib) that confers a therapeutic effect in a target patient population. The therapeutic effect may be objective (i.e., measurable by some test or marker) or subjective (i.e., subject gives an indication of or feels an effect). A "therapeutically effective amount" may be an amount effective to treat, ameliorate, or prevent a disease or condition, or to exhibit a detectable therapeutic or preventive effect, such as by ameliorating symptoms associated with the disease, preventing or delaying the onset of the disease or condition, and/or also lessening the severity or frequency of symptoms of the disease or condition. It should be understood that a therapeutically effective amount may not necessarily be effective in every subject treated with that amount. A therapeutically effective amount may be administered in a dosing regimen that comprises multiple doses. For any particular therapeutic agent, a therapeutically effective amount (and/or an appropriate unit dose within an effective dosing regimen) may vary, for example, depending on route of administration, or use in combination with other pharmaceutical agents. Also, the specific therapeutically effective amount (and/or unit dose) for any particular subject or patient population may depend upon a variety of factors including the disorder being treated and the severity of the disorder; the activity of the specific therapeutic agent employed; the specific composition employed; the age, body weight, general health, sex and diet of the subject; the time of administration, route of administration, and/or rate of excretion or metabolism of the specific therapeutic agent employed; the duration of the treatment; and like factors as is well known in the medical arts.

As used herein, the term "treat," "treating," or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat," "treating," or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to reducing the risk of or delaying the onset or development or progression of the disease or disorder.

2. Compositions

In one aspect of the present disclosure, a liquid pharmaceutical composition is provided comprising celecoxib, suspending agents, and a liquid carrier. In certain embodiments, a liquid pharmaceutical composition as described herein comprises celecoxib, suspending agents comprising xanthan gum and a synthetic magnesium aluminometasilicate, and a liquid carrier. In certain embodiments, the liquid pharmaceutical compositions described herein are formulated for oral use, i.e., they are oral liquid pharmaceutical compositions.

The concentration of celecoxib in a liquid pharmaceutical composition as described herein may be from 0.01 mg/mL to 100 mg/mL, e.g., from 0.01 mg/mL to 90 mg/mL, from 0.01 mg/mL to 80 mg/mL, from 0.01 mg/mL to 70 mg/mL, from 0.01 mg/mL to 60 mg/mL, from 0.01 mg/mL to 50 mg/mL, from 0.01 mg/mL to 40 mg/mL, from 0.01 mg/mL to 30 mg/mL, from 0.01 mg/mL to 20 mg/mL, or from 0.01 mg/mL to 10 mg/mL. For example, the concentration of celecoxib in a liquid pharmaceutical composition as described herein may be from 1 mg/mL to 50 mg/mL, e.g., from 1 mg/mL to 40 mg/mL, from 1 mg/mL to 30 mg/mL, from 1 mg/mL to 20 mg/mL, from 1 mg/mL to 15 mg/mL, or from 1 mg/mL to 10 mg/mL. In certain embodiments, the concentration of celecoxib in a liquid pharmaceutical composition as described herein is from 5 mg/mL to 50 mg/mL, e.g., from 5 mg/mL to 40 mg/mL, from 5 mg/mL to 30 mg/mL, from 5 mg/mL to 20 mg/mL, from 5 mg/mL to 15 mg/mL, or from 5 mg/mL to 10 mg/mL. In certain embodiments, the concentration of celecoxib in a liquid pharmaceutical composition as described herein is 10 mg/mL.

In any embodiments of the compositions described herein, the celecoxib may be celecoxib polymorphic Form III. Processes for preparing Form III celecoxib are known, e.g., as described in WO 2011/055233. Celecoxib polymorphic Forms I, II, and IV are all less stable than celecoxib Form III. Such forms require extreme conditions of heating, the use of solvents for crystallization, grinding or milling, or in the case of Form IV, must be precipitated in the presence of specific excipients to be generated from the more thermodynamically stable Form III. Thus, the celecoxib formulated in the liquid compositions described herein typically will be celecoxib polymorphic Form III.

In certain embodiments, the celecoxib is substantially pure celecoxib polymorphic Form III. The term "substantially pure celecoxib polymorphic Form III" refers to celecoxib polymorphic Form III having a purity of at least 99% as measured by HPLC, e.g., at least 99.5%, at least 99.8%, or at least 99.9%.

In certain embodiments, the celecoxib polymorphic Form III is free from other solid state forms of celecoxib. The term "free from other solid state forms" refers to the polymorphic Form III of celecoxib containing less than about 5% of other solid state forms of celecoxib, including less than 5%. In some embodiments, the polymorphic Form III of celecoxib contains less than 1% of other solid state forms of celecoxib.

In certain embodiments, the celecoxib polymorphic Form III is essentially free of other solid state forms of celecoxib. "Essentially free of other solid state forms of celecoxib" means that no other solid state forms of celecoxib can be detected within the limits of a powder X-ray diffractometer. "Other solid state forms of celecoxib" means forms other than Form III of celecoxib, including amorphous celecoxib.

A liquid pharmaceutical composition as described herein may be in the form of a suspension. In suspension embodiments, the celecoxib may be undissolved in the suspension.

A liquid pharmaceutical composition as described herein in the form of a suspension may comprise particles of celecoxib and one or more suspending agents.

In certain embodiments, a suspension as described herein comprises particles comprising celecoxib having article size distribution with a D10 of from 1 to 5 μm, a D50 from 8 to 12 μm, and a D90 from 20 to 26 μm. In certain embodiments, a suspension as described herein comprises particles containing celecoxib having a particle size distribution with a D10 of not less than (NLT) 1 μm, a D50 from 5 μm to 12.5 μm, and a D90 of not more than (NMT) 30 μm. In certain embodiments, a suspension as described herein comprises articles comprising celecoxib having a particle size distribution with a D10 of NLT 3 μm, a D50 from 7 μm to 11 μm, and a D90 of NMT 25 μm. The particle size can be determined by means of laser diffractometry.

As noted above, the liquid pharmaceutical compositions of the present disclosure may comprise one or more suspending agents, particularly xanthan gum and synthetic magnesium aluminometasilicate. In certain embodiments, a liquid pharmaceutical composition as described herein comprises suspending agents, wherein the suspending agents consist essentially of xanthan gum and a synthetic magnesium aluminometasilicate. For example, suspending agents consisting essentially of xanthan gum and a synthetic magnesium aluminometasilicate refers to suspending agents that do not contain purified magnesium aluminum silicates. In certain embodiments, a liquid pharmaceutical composition as described herein comprises suspending agents, wherein the suspending agents consist of xanthan gum and a synthetic magnesium aluminometasilicate. The suspending agents (e.g., xanthan gum and synthetic magnesium aluminometasilicate) may be used in any amount(s) effective to achieve the desired effect, e.g., any amount(s) effective to stabilize the suspension against one or more of aggregation and settling of the celecoxib. Exemplary suitable amounts are described in more detail below, and include, for example, from 0.2% w/v to 2% w/v xanthan gum and from 0.05% w/v to 2% w/v of a synthetic magnesium aluminometasilicate.

Synthetic magnesium aluminometasilicate has the molecular formula $Al_2O_3 \cdot MgO \cdot 1.7SiO_2 \cdot xH_2O$. The synthetic magnesium aluminometasilicate may comprise from 29.1 to 35.5% $Al_2O_3$ by weight on a dry basis; from 11.4 to 14.0% MgO by weight on a dry basis, and from 29.2 to 35.6 $SiO_2$ by weight on a dry basis. The synthetic magnesium aluminometasilicate may be amorphous. The synthetic magnesium aluminometasilicate may be neutral (i.e., a 2 g sample added to 50 mL of water and allowed to stand for 2 minutes has a pH from 6.0-8.0). The synthetic magnesium aluminometasilicate may have a loose bulk density from 0.06 to 0.11 g/mL. The synthetic magnesium aluminometasilicate may have a tapped bulk density from 0.1 to 0.17 g/mL. The synthetic magnesium aluminometasilicate may have an average particle size from 2.5 to 3.5 μm. In certain embodiments, the synthetic magnesium aluminometasilicate has an average particle size of 3.1 μm. In certain embodiments, the synthetic magnesium aluminometasilicate has one or more of the above features. In certain embodiments, the synthetic magnesium aluminometasilicate has all of the above features. In certain embodiments, the synthetic magnesium aluminometasilicate is, or is identical to, the synthetic magnesium aluminometasilicate product Neusilin® ULF2 (CAS No. 12511-31-8), sold by Fuji Chemical Industries.

Synthetic magnesium aluminometasilicate is distinct both physically and chemically from purified natural magnesium aluminum silicates, such as purified bentonites (e.g., Veegum® HS, Vanderbilt Minerals, LLC) and purified smectite clays (e.g., Veegum® HV, Vanderbilt Minerals, LLC). In certain embodiments, the liquid pharmaceutical compositions as described herein do not contain purified magnesium aluminum silicates.

The amount of synthetic magnesium aluminometasilicate in a liquid pharmaceutical composition as described herein may be from 0.05% w/v to 2% w/v, e.g., from 0.05% w/v to 1.5% w/v, from 0.05% w/v to 1% w/v, from 0.05% w/v to 0.75% w/v, from 0.05% w/v to 0.5% w/v, or from 0.05% w/v to 0.25% w/v. In certain embodiments, the amount of synthetic magnesium aluminometasilicate in a liquid pharmaceutical composition as described herein is from 0.1% w/v to 2% w/v, e.g., from 0.1% w/v to 1.5% w/v, from 0.1% w/v to 1% w/v, from 0.1% w/v to 0.75% w/v, from 0.1% w/v to 0.5% w/v, or from 0.1% w/v to 0.25% w/v. In certain embodiments, the amount of synthetic magnesium aluminometasilicate in a liquid pharmaceutical composition as described herein is from 0.1% w/v to 0.75% w/v, e.g., from 0.1% w/v to 0.7% w/v, from 0.1% w/v to 0.65% w/v, from 0.1% w/v to 0.6% w/v, from 0.1% w/v to 0.55% w/v, or from 0.1% w/v to 0.5% w/v. In certain embodiments, the amount of synthetic magnesium aluminometasilicate in a liquid pharmaceutical composition as described herein is from 0.2% w/v to 0.75% w/v, e.g., from 0.2% w/v to 0.7% w/v, from 0.2% w/v to 0.65% w/v, from 0.2% w/v to 0.6% w/v, from 0.2% w/v to 0.55% w/v, or from 0.2% w/v to 0.5% w/v.

In certain embodiments, the weight ratio of xanthan gum to synthetic magnesium aluminometasilicate in a liquid pharmaceutical composition as described herein is from 2:1 to 1:2, e.g., from 2:1 to 1:1 or from 1:1 to 1:2. In certain embodiments, the weight ratio of xanthan gum to synthetic magnesium aluminometasilicate is 1:1.

The amount of xanthan gum in a liquid pharmaceutical composition as described herein may be from 0.2% w/v to 2% w/v, e.g., from 0.2% w/v to 1.5% w/v, from 0.2% w/v to 1% w/v, from 0.2% w/v to 0.75% w/v, or from 0.2% w/v to 0.5% w/v. In certain embodiments, the amount of xanthan gum in a liquid pharmaceutical composition as described herein is from 0.5% w/v to 2% w/v, e.g., from 0.5% w/v to 1.5% w/v, from 0.5% w/v to 1% w/v, or from 0.5% w/v to 0.75% w/v. In certain embodiments, the amount of xanthan gum in the liquid pharmaceutical composition is from above 0.25% w/v to 2% w/v, e.g., from above 0.25% w/v to 1.5% w/v, from above 0.25% w/v to 1% w/v, from above 0.25% w/v to 0.75% w/v, or from above 0.25% w/v to 0.5% w/v. In certain embodiments, the amount of xanthan gum in a liquid pharmaceutical composition as described herein is from 0.2% w/v to 0.75% w/v, from 0.2% w/v to 0.7% w/v, from 0.2% w/v to 0.6% w/v, from 0.25% w/v to 0.75% w/v, from 0.25% w/v to 0.7% w/v, or from 0.25% w/v to 0.6% w/v.

A liquid pharmaceutical composition as described herein may further comprise one or more pharmaceutically acceptable excipients, optionally including one or more selected from preservatives, sweetening agents, buffering agents, coloring agents, flavoring agents, and pH modifiers.

In certain embodiments, a liquid pharmaceutical composition as described herein comprises at least one preservative.

In certain embodiments, a liquid pharmaceutical composition as described herein comprises a preservative selected from a quaternary ammonium compound (such as benzalkonium chloride, benzethonium chloride, cetrimide, cetylpyridinium chloride, lauralkonium chloride and myristyl picolinium chloride), a mercurial agent (such as phenylmercuric nitrate, phenylmercuric acetate, and thimerosal), an alcoholic agent (such as chlorobutanol, phenylethyl alcohol and benzyl alcohol), an antibacterial ester (such as esters of p-hydroxybenzoic acid), a chelating agent (such as disodium edetate (EDTA)), chlorhexidine, chlorocresol, sorbic acid, potassium sorbate, a benzoate (such as sodium benzoate), a propionate (such as sodium proprionate), methylparaben, ethylparaben, propylparaben, butylparaben paraben, sulfur dioxide, sulfite, nitrite, nitrate, lactic acid, propionic acid, propionate, ascorbic acid, ascorbate, butylated hydroxytoluene (BHT), hydroxyanisole, propyl gallate, lavender, thyme, peppermint, cajuput, cinnamon, clove, eucalyptus, sage, tea tree, salts of the foregoing, and combinations thereof. In certain embodiments, the preservative is selected from benzyl alcohol, methyl paraben, propyl paraben, butyl paraben, ethyl paraben, sorbic acid, potassium sorbate, benzalkonium chloride, benzoic acid, sodium benzoate, and combinations thereof. In certain embodiments, the preservative comprises one or both of methyl paraben and propyl paraben, including both methyl paraben and propyl paraben.

When used, a liquid pharmaceutical composition as described herein may comprise from 0.001% to 5% w/v of the at least one preservative, e.g., from 0.001% w/v to 4% w/v, from 0.001% w/v to 3% w/v, from 0.001% w/v to 2% w/v, from 0.001% w/v to 1% w/v, from 0.001% w/v to 0.1% w/v, from 0.001% w/v to 0.01% w/v, from 0.01% w/v to 5% w/v, from 0.01% w/v to 4% w/v, from 0.01% w/v to 3% w/v, from 0.01% w/v to 2% w/v, from 0.01% w/v to 1% w/v, from 0.01% w/v to 0.1% w/v, from 0.1% w/v to 5% w/v, from 0.1% w/v to 4% w/v, from 0.1% w/v to 3% w/v, from 0.1% w/v to 2% w/v, from 0.1% w/v to 1% w/v, from 1% w/v to 5% w/v, from 1% w/v to 4% w/v, from 1% w/v to 3% w/v, or from 1% w/v to 2% w/v. In certain embodiments, the liquid pharmaceutical composition comprises from 0.01% w/v to 1% w/v of the at least one preservative, e.g., from 0.01% to 0.75% w/v, from 0.01% w/v to 0.5% w/v, or from 0.01% w/v to 0.25% w/v. In certain embodiments, the liquid pharmaceutical composition comprises from 0.05% w/v to 0.5% w/v of the at least one preservative. In certain embodiments, the liquid pharmaceutical composition comprises from 0.05% w/v to 0.5% w/v of a mixture of methyl paraben and propyl paraben.

In certain embodiments, a liquid pharmaceutical composition comprises at least one buffering agent.

In certain embodiments, the buffering agent is selected from citric acid, sodium citrate dihydrate, citric acid monohydrate, phosphoric acid, succinic acid, tartaric acid, lactic acid, acetic acid and salts thereof, sodium hydroxide, sodium phosphate, disodium hydrogen phosphate, sodium hydrogen carbonate, monosodium phosphate, monopotassium phosphate, dipotassium phosphate, potassium citrate, gluconic acid and salts thereof, and combinations thereof. In certain embodiments, the buffering agent comprises one or both of citric acid and sodium citrate dihydrate, including citric acid and sodium citrate dihydrate.

When present, a liquid pharmaceutical composition as described herein may comprise from 0.001% w/v to 5% w/v of the at least one buffering agent, e.g., from 0.001% w/v to 4% w/v, from 0.001% w/v to 3% w/v, from 0.001% w/v to 2% w/v, from 0.001% w/v to 1% w/v, from 0.001% w/v to 0.01% w/v, or from 0.001% w/v to 0.1% w/v. In certain embodiments, the liquid pharmaceutical composition comprises from 0.1% w/v to 2% w/v of the at least one buffering agent, e.g., from 0.1% w/v to 1.5% w/v, from 0.1% w/v to 1% w/v, or from 0.1% w/v to 0.5% w/v. In certain embodiments, the liquid pharmaceutical composition comprises from 0.1% w/v to 2% w/v of a mixture of citric acid and sodium citrate dihydrate, e.g., from 0.1% w/v to 1.5% w/v, from 0.1% w/v to 1% w/v, or from 0.1% w/v to 0.5% w/v.

In certain embodiments, a liquid pharmaceutical composition as described herein comprises at least one sweetening agent.

In certain embodiments, the sweetening agent is a natural sweetener, e.g., fructose, sucrose, glucose, and sugar alcohols such as erythritol, mannitol, sorbitol, xylitol, lactitol, isomalt, and maltitol.

In certain embodiments, the sweetening agent is a high potency sweetener, e.g., sodium saccharin, potassium saccharin, sodium cyclamate, aspartame, thaumatin, acesulfame potassium, sucralose, alitame, neotame, xylose, ribose, mannose, galactose, neohesperidin dihydrochalcone, stevia sweeteners, monk fruit sweeteners, and combinations thereof. In certain embodiments, the sweetening agent is sucralose.

When used, any suitable amount of sweetening agent may be used, which may vary on the specific sweeting agent(s) used, e.g., depending on whether a natural sweetener or high potency sweetener is used. In certain embodiments, the sweetening agent comprises a mixture of at least one natural sweetener and at least one high potency sweetener.

In certain embodiments, a liquid pharmaceutical composition as described herein comprises from 0.001% w/v to 5% w/v of a high potency sweetener, e.g., from 0.001% w/v to 4% w/v, from 0.001% w/v to 3% w/v, from 0.001% w/v to 2% w/v, from 0.001% w/v to 1% w/v, from 0.001% w/v to 0.01% w/v, or from 0.001% w/v to 0.1% w/v. In certain embodiments, the liquid pharmaceutical composition comprises from 0.01% w/v to 1% w/v of a high potency sweetener, e.g., from 0.01% w/v to 0.75% w/v, from 0.01% w/v to 0.5% w/v, from 0.01% w/v to 0.25% w/v, from 0.1% w/v to 1% w/v, from 0.1% w/v to 0.75% w/v, from 0.1% w/v to 0.5% w/v, or from 0.1% w/v to 0.25% w/v. In certain embodiments, the liquid pharmaceutical composition comprises from 0.05% w/v to 0.5% w/v of a high potency sweetener. In certain embodiments, the liquid pharmaceutical composition comprises from 0.05% w/v to 0.5% w/v of sucralose.

In certain embodiments, a liquid pharmaceutical composition as described herein comprises from 0.001% w/v to 85% w/v of a natural sweetener, e.g., from 0.1% w/v to 85% w/v, from 1% w/v to 85% w/v, from 10% w/v to 85% w/v, from 25% w/v to 85% w/v, or from 50% w/v to 85% w/v.

A liquid pharmaceutical composition as described herein may comprise at least one pH modifier to adjust the pH to the desired level at the end of manufacture. In certain embodiments, the pH modifier is selected from sodium hydroxide, hydrochloric acid, or a combination thereof.

A liquid pharmaceutical composition as described herein may comprise a liquid carrier comprising water. In certain embodiments, the liquid pharmaceutical composition comprises a liquid carrier comprising water and a wetting agent for celecoxib.

A liquid pharmaceutical composition as described herein may comprise from 50% w/v to 95% w/v water, e.g., from 50% w/v to 90% w/v, from 50% w/v to 85% w/v, from 50% w/v to 80% w/v, from 50% w/v to 75% w/v, from 50% w/v to 70% w/v, from 50% w/v to 65% w/v, from 50% w/v to 55% w/v, from 60% w/v to 95% w/v, from 60% w/v to 90% w/v, from 60% w/v to 85% w/v, from 60% w/v to 80% w/v, from 60% w/v to 75% w/v, from 60% w/v to 70% w/v, from 60% w/v to 65% w/v, from 70% w/v to 95% w/v, from 70% w/v to 90% w/v, from 70% w/v to 85% w/v, from 70% w/v to 80% w/v, from 70% w/v to 75% w/v, from 80% w/v to 95% w/v, from 80% w/v to 90% w/v, from 80% w/v to 85% w/v, or from 90% w/v to 95% w/v. In certain embodiments, the liquid pharmaceutical composition comprises from 80% w/v to 90% w/v water.

In certain embodiments, a liquid pharmaceutical composition as described herein comprises a liquid carrier comprising at least one wetting agent (e.g., for celecoxib).

The wetting agent may be selected from glycols, glycol ether, glycerin, polyoxyethylene alcohols, polyoxyethylene fatty acid esters, and combinations thereof. In certain embodiments, the wetting agent comprises glycerin. In certain embodiments, the wetting agent consists of glycerin. In certain embodiments, the liquid pharmaceutical composition does not contain propylene glycol.

When used, a liquid pharmaceutical composition as described herein may comprise from 1% w/v to 30% w/v of at least one wetting agent, e.g., from 1% w/v to 25% w/v, from 1% w/v to 20% w/v, from 1% w/v to 15% w/v, from 1% w/v to 10% w/v, from 1% w/v to 5% w/v, from 5% w/v to 30% w/v, from 5% w/v to 25% w/v, from 5% w/v to 20% w/v, from 5% w/v to 15% w/v, from 5% w/v to 10% w/v, from 10% w/v to 30% w/v, from 10% w/v to 25% w/v, from 10% w/v to 20% w/v, from 10% w/v to 15% w/v, from 15% w/v to 30% w/v, from 15% w/v to 25% w/v, from 15% w/v to 20% w/v, from 20% w/v to 30% w/v, from 20% w/v to 25% w/v, or from 25% w/v to 30% w/v. In certain embodiments, the liquid pharmaceutical composition comprises from 10% to 20% w/v of at least one wetting agent. In certain embodiments, the liquid pharmaceutical composition comprises from 10% to 20% w/v of glycerin.

In certain embodiments, a liquid pharmaceutical composition as described herein comprises from 0.01 mg/mL to 100 mg/mL celecoxib, suspending agents comprising from 0.2% w/v to 2% w/v xanthan gum and from 0.05% w/v to 2% w/v of a synthetic magnesium aluminometasilicate, and a liquid carrier comprising water and at least one wetting agent. The liquid pharmaceutical composition optionally further comprises one or more preservatives, buffering agents and sweetening agents.

In certain embodiments, a liquid pharmaceutical composition as described herein comprises from 0.01 mg/mL to 100 mg/mL celecoxib, suspending agents comprising from 0.2% w/v to 2% w/v xanthan gum and from 0.05% w/v to 2% w/v of a synthetic magnesium aluminometasilicate, and a liquid carrier comprising water and glycerin. The liquid pharmaceutical composition optionally further comprises one or more preservatives comprising methyl paraben and propyl paraben, buffering agents comprising citric acid and sodium citrate dihydrate, and sweetening agents comprising sucralose.

In certain embodiments, a liquid pharmaceutical composition as described herein comprises from 0.01 mg/mL to 100 mg/mL celecoxib; suspending agents comprising from 0.2% w/v to 2% w/v xanthan gum and from 0.05% w/v to 2% w/v of a synthetic magnesium aluminometasilicate; from 0.001% w/v to 5% w/v of a preservative; from 0.001% w/v to 5% w/v of a buffering agent; from 0.001% w/v to 5% w/v of a sweetening agent; and a liquid carrier comprising water and from 1% w/v to 30% w/v of a wetting agent.

In certain embodiments, a liquid pharmaceutical composition as described herein comprises from 0.01 mg/mL to 100 mg/mL celecoxib; suspending agents comprising from 0.2% w/v to 2% w/v xanthan gum and from 0.05% w/v to 2% w/v of a synthetic magnesium aluminometasilicate; from 0.001% w/v to 5% w/v of a preservative; from 0.001% w/v to 5% w/v of a buffering agent; from 0.001% w/v to 5% w/v of a sweetening agent; and a liquid carrier comprising from 50% w/v to 95% w/v water and from 1% w/v to 30% w/v of a wetting agent.

In certain embodiments, a liquid pharmaceutical composition as described herein comprises from 0.01 mg/mL to 100 mg/mL celecoxib; suspending agents comprising from 0.2% w/v to 2% w/v xanthan gum and from 0.05% w/v to 2% w/v of a synthetic magnesium aluminometasilicate; from 0.001% w/v to 5% w/v of a preservative comprising methyl paraben and propyl paraben; from 0.001% w/v to 5% w/v of a buffering agent comprising citric acid and sodium citrate dihydrate; from 0.001% w/v to 5% w/v of a sweetening agent comprising sucralose; and a liquid carrier comprising water and from 1% w/v to 30% w/v of a wetting agent comprising glycerin.

In certain embodiments, a liquid pharmaceutical composition as described herein comprises from 0.01 mg/mL to 100 mg/mL celecoxib; suspending agents comprising from 0.2% w/v to 2% w/v xanthan gum and from 0.05% w/v to 2% w/v of a synthetic magnesium aluminometasilicate; from 0.001% w/v to 5% w/v of a preservative comprising methyl paraben and propyl paraben; from 0.001% w/v to 5% w/v of a buffering agent comprising citric acid and sodium citrate dihydrate; from 0.001% w/v to 5% w/v of a sweetening agent comprising sucralose; and a liquid carrier comprising from 50% w/v to 95% w/v water and from 1% w/v to 30% w/v of a wetting agent comprising glycerin.

In certain embodiments, a liquid pharmaceutical composition as described herein comprises from 1 mg/mL to 20 mg/mL celecoxib, suspending agents comprising from 0.25% w/v to 0.75% w/v xanthan gum and from 0.2% w/v to 0.6% w/v of a synthetic magnesium aluminometasilicate, and a liquid carrier comprising water and at least one wetting agent. The liquid pharmaceutical composition optionally further comprises one or more preservatives, buffering agents and sweetening agents.

In certain embodiments, a liquid pharmaceutical composition as described herein comprises from 1 mg/mL to 20 mg/mL celecoxib, suspending agents comprising from 0.25% w/v to 0.75% w/v xanthan gum and from 0.2% w/v to 0.6% w/v of a synthetic magnesium aluminometasilicate, and a liquid carrier comprising water and glycerin. The liquid pharmaceutical composition optionally further comprises one or more preservatives comprising methyl paraben and propyl paraben, buffering agents comprising citric acid and sodium citrate dihydrate, and sweetening agents comprising sucralose.

In certain embodiments, a liquid pharmaceutical composition as described herein comprises from 1 mg/mL to 20 mg/mL celecoxib; suspending agents comprising from 0.25% w/v to 0.75% w/v xanthan gum and from 0.2% w/v to 0.6% w/v of a synthetic magnesium aluminometasilicate; from 0.01% w/v to 1% w/v of a preservative; from 0.1% w/v to 2% w/v of a buffering agent; from 0.01% w/v to 1% w/v of a sweetening agent; and a liquid carrier comprising water and from 1% w/v to 20% w/v of a wetting agent.

In certain embodiments, a liquid pharmaceutical composition as described herein comprises from 1 mg/mL to 20 mg/mL celecoxib; suspending agents comprising from 0.25% w/v to 0.75% w/v xanthan gum and from 0.2% w/v to 0.6% w/v of a synthetic magnesium aluminometasilicate; from 0.01% w/v to 1% w/v of a preservative; from 0.1% w/v to 2% w/v of a buffering agent; from 0.01% w/v to 1% w/v of a sweetening agent; and a liquid carrier comprising from 80% w/v to 95% w/v water and from 1% w/v to 20% w/v of a wetting agent.

In certain embodiments, a liquid pharmaceutical composition as described herein comprises from 1 mg/mL to 20 mg/mL celecoxib; suspending agents comprising from 0.25% w/v to 0.75% w/v xanthan gum and from 0.2% w/v to 0.6% w/v of a synthetic magnesium aluminometasilicate; from 0.01% w/v to 1% w/v of a preservative comprising methyl paraben and propyl paraben; from 0.1% w/v to 2% w/v of a buffering agent comprising citric acid and sodium citrate dihydrate; from 0.01% w/v to 1% w/v of a sweetening agent comprising sucralose; and a liquid carrier comprising from water and from 1% w/v to 20% w/v of a wetting agent comprising glycerin.

In certain embodiments, a liquid pharmaceutical composition as described herein comprises from 1 mg/mL to 20 mg/mL celecoxib; suspending agents comprising from 0.25% w/v to 0.75% w/v xanthan gum and from 0.2% w/v to 0.6% w/v of a synthetic magnesium aluminometasilicate; from 0.01% w/v to 1% w/v of a preservative comprising methyl paraben and propyl paraben; from 0.1% w/v to 2% w/v of a buffering agent comprising citric acid and sodium citrate dihydrate; from 0.01% w/v to 1% w/v of a sweetening agent comprising sucralose; and a liquid carrier comprising from 80% w/v to 95% w/v water and from 1% w/v to 20% w/v of a wetting agent comprising glycerin.

In certain embodiments, a liquid pharmaceutical composition as described herein comprises 10 mg/mL celecoxib, suspending agents comprising 0.5% w/v xanthan gum and 0.5% w/v of a synthetic magnesium aluminometasilicate, and a liquid carrier comprising water and at least one wetting agent. The liquid pharmaceutical composition optionally further comprises one or more preservatives, buffering agents, and sweetening agents.

In certain embodiments, a liquid pharmaceutical composition as described herein comprises 10 mg/mL celecoxib, suspending agents comprising 0.5% w/v xanthan gum and 0.5% w/v of a synthetic magnesium aluminometasilicate, and a liquid carrier comprising water and glycerin. The liquid pharmaceutical composition optionally further comprises one or more preservatives comprising methyl paraben and propyl paraben, buffering agents comprising citric acid and sodium citrate dihydrate, and sweetening agents comprising sucralose.

In certain embodiments, a liquid pharmaceutical composition as described herein comprises 10 mg/mL celecoxib; suspending agents comprising 0.5% w/v xanthan gum and 0.5% w/v of a synthetic magnesium aluminometasilicate; from 0.05% w/v to 0.5% w/v of a preservative; from 0.1% w/v to 2% w/v of a buffering agent; from 0.05% w/v to 0.5% w/v of a sweetening agent; and a liquid carrier comprising water and from 10% w/v to 20% w/v of a wetting agent.

In certain embodiments, a liquid pharmaceutical composition as described herein comprises 10 mg/mL celecoxib; suspending agents comprising 0.5% w/v xanthan gum and 0.5% w/v of a synthetic magnesium aluminometasilicate; from 0.05% w/v to 0.5% w/v of a preservative; from 0.1% w/v to 2% w/v of a buffering agent; from 0.05% w/v to 0.5% w/v of a sweetening agent; and a liquid carrier comprising from 80% w/v to 90% w/v water and from 10% w/v to 20% w/v of a wetting agent.

In certain embodiments, a liquid pharmaceutical composition as described herein comprises 10 mg/mL celecoxib; suspending agents comprising 0.5% w/v xanthan gum and 0.5% w/v of a synthetic magnesium aluminometasilicate; from 0.05% w/v to 0.5% w/v of a preservative comprising methyl paraben and propyl paraben; from 0.1% w/v to 2% w/v of a buffering agent comprising citric acid and sodium citrate dihydrate; from 0.05% w/v to 0.5% w/v of a sweetening agent comprising sucralose; and a liquid carrier comprising water and from 10% w/v to 20% w/v of a wetting agent comprising glycerin.

In certain embodiments, a liquid pharmaceutical composition as described herein comprises 10 mg/mL celecoxib; suspending agents comprising 0.5% w/v xanthan gum and 0.5% w/v of a synthetic magnesium aluminometasilicate; from 0.05% w/v to 0.5% w/v of a preservative comprising methyl paraben and propyl paraben; from 0.1% w/v to 2% w/v of a buffering agent comprising citric acid and sodium citrate dihydrate; from 0.05% w/v to 0.5% w/v of a sweetening agent comprising sucralose; and a liquid carrier comprising from 80% w/v to 90% w/v water and from 10% w/v to 20% w/v of a wetting agent comprising glycerin.

In certain embodiments, a liquid pharmaceutical composition as described herein does not contain sodium lauryl sulfate. In certain embodiments, the liquid pharmaceutical composition as described herein does not contain propylene glycol. In certain embodiments, the liquid pharmaceutical composition does not contain purified (natural) magnesium aluminum silicate. In certain embodiments, a liquid pharmaceutical composition as described herein does not contain sodium lauryl sulfate and does not contain propylene glycol and does not contain purified (natural) magnesium aluminum silicate.

(a) Properties

The pH of the compositions described herein may be any suitable pH, such as any pH suitable for oral administration at which the composition exhibits acceptable stability. For example, a liquid pharmaceutical composition as described herein may have a pH from 3 to 9, e.g., from 3 to 8, from 3 to 7, from 3 to 6, from 3 to 5, from 3 to 4, from 4 to 9, from 4 to 8, from 4 to 7, from 4 to 6, from 4 to 5, from 5 to 9, from 5 to 8, from 5 to 7, from 5 to 6, from 6 to 9, from 6 to 8, from 6 to 7, from 7 to 9, from 7 to 8, or from 8 to 9. In certain embodiments, the liquid pharmaceutical composition has a pH from 4 to 6 or from 4.5 to 5.5. In certain embodiments, the liquid pharmaceutical composition has a pH above 5.2, e.g., from above 5.2 to 8, from above 5.2 to 6, or from above 5.2 to 5.5. As noted above, a liquid pharmaceutical composition as described herein may comprise a pH modifier to adjust the pH to a desired level, such as sodium hydroxide, hydrochloric acid, or a combination thereof.

In certain embodiments, the liquid pharmaceutical compositions of the present disclosure exhibit improved stability over other celecoxib-containing liquid compositions. One measure of stability is the change in pH over time following preparation of the liquid composition. In certain embodiments, the pH of the liquid pharmaceutical compositions of the present disclosure is stable over time, e.g., when stored under room temperature conditions.

In certain embodiments, the pH of the liquid pharmaceutical composition does not change by more than 0.5 pH units following storage at 25° C. for at least one month, at least three months, at least six months, or at least 12 months. In certain embodiments, the pH of the liquid pharmaceutical composition does not change by more than 0.4 pH units following storage at 25° C. for at least one month, at least three months, at least six months, or at least 12 months. In certain embodiments, the pH of the liquid pharmaceutical composition does not change by more than 0.2 pH units following storage at 25° C. for at least one month, at least three months, at least six months, or at least 12 months. In certain embodiments, the pH of the liquid pharmaceutical composition does not change by more than 0.1 pH unit following storage at 25° C. for at least one month, at least three months, at least six months, or at least 12 months.

In certain embodiments, the pH of the liquid pharmaceutical composition does not change by more than 0.5 pH units following storage at 40° C. for at least one month, at least three months, at least six months, or at least 12 months. In certain embodiments, the pH of the liquid pharmaceutical composition does not change by more than 0.4 pH units following storage at 40° C. for at least one month, at least three months, at least six months, or at least 12 months. In certain embodiments, the pH of the liquid pharmaceutical composition does not change by more than 0.2 pH units following storage at 40° C. for at least one month, at least three months, at least six months, or at least 12 months. In certain embodiments, the pH of the liquid pharmaceutical composition does not change by more than 0.1 pH unit following storage at 40° C. for at least one month, at least three months, at least six months, or at least 12 months.

In certain embodiments of the compositions described herein in the form of a suspension (e.g., "suspension compositions") exhibit good properties with regard to uniformity and dispersibility of celecoxib following storage at 25° C. or 40° C. in a closed bottle stored in an upright or horizontal orientation. In certain embodiments, a suspension composition as described herein exhibits less than a 5% difference in celecoxib content between the top and bottom of the composition following storage in a closed bottle at 25° C. in an upright or horizontal orientation for a period of time, wherein celecoxib content is measured following shaking the bottle for 30 seconds, including a difference of less than 4%, less than 3%, less than 2% or less than 1%, wherein the period of time may be selected from at least three months, at least six months, at least one year, at least 18 months, or at least 2 years. In certain embodiments, a suspension composition as described herein exhibits less than a 5% difference in celecoxib content between the top and bottom of the composition following storage in a closed bottle at 40°

C. in an upright or horizontal orientation for a period of time, wherein celecoxib content is measured following shaking the bottle for 30 seconds, including a difference of less than 4%, less than 3%, less than 2% or less than 1%, wherein the period of time may be selected from at least three months, at least six months, at least one year, at least 18 months, or at least 2 years.

In certain embodiments, a suspension composition as described herein exhibits less than a 5% difference in celecoxib content between the top and bottom of the composition following storage in a closed bottle at 25° C. in an upright or horizontal orientation for a period of time, wherein celecoxib content is measured without shaking the bottle prior to measurement, including a difference of less than 4%, less than 3%, less than 2% or less than 1%, wherein the period of time may be selected from at least three months, at least six months, at least one year, at least 18 months, or at least 2 years.

In certain embodiments, the liquid pharmaceutical compositions of the present disclosure exhibit advantageous celecoxib release profiles. In certain embodiments, a liquid pharmaceutical composition as described herein exhibits the following average celecoxib release profile when at least 12 samples are evaluated under the Dissolution Test Conditions set forth below:

(a) from 5% to 45% celecoxib release in 5 minutes,
(b) from 15% to 50% celecoxib release in 10 minutes,
(c) from 30% to 75% celecoxib release in 15 minutes,
(d) from 55% to 85% celecoxib release in 20 minutes, and
(e) greater than 80% celecoxib release in 30 minutes In certain embodiments, a liquid pharmaceutical composition as described herein exhibits the following average celecoxib release profile when at least 12 samples are evaluated under Dissolution Test Conditions:

(a) from 5% to 25% celecoxib release in 5 minutes,
(b) from 26% to 35% celecoxib release in 10 minutes,
(c) from 40% to 60% celecoxib release in 15 minutes,
(d) from 62% to 80% celecoxib release in 20 minutes, and
(e) greater than 85% celecoxib release in 30 minutes

| Dissolution Test Conditions | |
|---|---|
| Media | 0.04M Sodium Phosphate Tribasic, pH adjusted to 11.1 with $H_3PO_4$, with a sodium dodecyl sulfate (SDS) concentration of 0.5% |
| Media Volume | 1000 mL |
| Paddle Speed | 75 rpm |
| Media Temperature | 37° C. |

In certain embodiments, the liquid pharmaceutical compositions of the present disclosure are bioequivalent to capsule formulations of celecoxib (e.g., CELEBREX®) when administered orally at equivalent doses from 50 to 200 mg, e.g., 200 mg. In certain embodiments, a liquid pharmaceutical composition as described herein is in the form of a suspension according to Table A, and is bioequivalent to capsule formulations of celecoxib (e.g., CELEBREX®) when administered orally at equivalent doses from 50 to 200 mg, e.g., 200 mg:

TABLE A

| Ingredient | Amount (% w/v) |
|---|---|
| Celecoxib | 1 |
| Xanthan Gum | 0.5 |
| Synthetic Magnesium Aluminometasilicate | 0.5 |
| Citric Acid Anhydrous | 0.7 |
| Sodium Citrate Dihydrate | 1.1 |
| Methylparaben | 0.15 |
| Propylparaben | 0.05 |
| Sucralose | 0.1 |
| Glycerin | 15.0 |
| Purified Water | QS |
| Total | 100% |

The capsule formulations of celecoxib (e.g., CELEBREX®) may have the components of Table B (filled into capsules):

TABLE B

| Ingredients |
|---|
| Celecoxib |
| Croscarmellose sodium |
| Edible inks |
| Gelatin |
| Lactose monohydrate |
| Magnesium stearate |
| Povidone |
| Sodium lauryl sulfate |

In certain embodiments, the liquid pharmaceutical compositions of the present disclosure exhibit improved acid neutralizing capacity over other celecoxib-containing liquid formulations.

In certain embodiments, a liquid pharmaceutical composition as described herein has an acid neutralizing capacity from 2 to 5 mEq per 200 mg dose, e.g., from 2 to 4.5 mEq per 200 mg dose, from 2 to 4 mEq per 200 mg dose, from 2 to 3.5 mEq per 200 mg dose, from 2 to 3 mEq per 200 mg dose, from 2 to 2.5 mEq per 200 mg dose, from 3 to 5 mEq per 200 mg dose, from 3 to 4.5 mEq per 200 mg dose, from 3 to 4 mEq per 200 mg dose, from 3 to 3.5 mEq per 200 mg dose, from 4 to 5 mEq per 200 mg dose, or from 4.5 to 5 mEq per 200 mg dose. In certain embodiments, the liquid pharmaceutical composition has an acid neutralizing capacity from 2 to 3 mEq per 200 mg dose, e.g., from 2 to 2.75 mEq per 200 mg dose.

3. Methods of Preparing Liquid Pharmaceutical Compositions

In another aspect, the present disclosure provides methods of preparing the liquid pharmaceutical compositions described hereinabove.

A suitable method of preparing a liquid pharmaceutical composition described herein may comprise preparing a dispersion comprising celecoxib and suspending agents comprising xanthan gum and a synthetic magnesium aluminometasilicate in a wetting agent, adding the dispersion to a mixture comprising water and at least one water-soluble excipient and mixing to obtain the composition. In certain embodiments, a method comprises:

(a) dispersing celecoxib and suspending agents comprising xanthan gum and a synthetic magnesium aluminometasilicate in a wetting agent in a first vessel to obtain a dispersion;
(b) mixing water and at least one water-soluble excipient in a second vessel; and (c) adding the dispersion of the first vessel to the second vessel and mixing to obtain the liquid pharmaceutical composition.

The amount of celecoxib used in the methods can be any suitable amount, including amounts that would achieve the amounts described hereinabove for the compositions. In certain embodiments, an amount of celecoxib is used that will provide from 0.01 mg/mL to 100 mg/mL celecoxib in the final liquid pharmaceutical composition, e.g., the liquid pharmaceutical composition obtained at step (c). In certain embodiments, an amount of celecoxib is used that will provide from 1 mg/mL to 50 mg/mL celecoxib in the liquid pharmaceutical composition, e.g., 10 mg/mL.

In certain embodiments, the suspending agents consist essentially of xanthan gum and synthetic magnesium aluminometasilicate. In certain embodiments, the suspending agents consist of xanthan gum and synthetic magnesium aluminometasilicate. The amounts of xanthan gum and synthetic magnesium aluminometasilicate used in the methods can be any suitable amounts, including amounts that would achieve the amounts described hereinabove for the compositions. In certain embodiments, the amounts used will provide from 0.2% w/v to 2% w/v xanthan gum and from 0.05% w/v to 2% w/v synthetic magnesium aluminometasilicate in the final liquid pharmaceutical composition, e.g., the liquid pharmaceutical composition obtained at step (c). In certain embodiments, the amounts used will provide from 0.25% w/v to 0.75% w/v xanthan gum and from 0.2% w/v to 0.6% w/v synthetic magnesium aluminometasilicate in the final liquid pharmaceutical composition, such as 0.5% w/v xanthan gum and 0.5% w/v synthetic magnesium aluminometasilicate. In certain embodiments, the amount of synthetic magnesium aluminometasilicate used provides from 0.2% w/v to 0.75% w/v synthetic magnesium aluminometasilicate in the final liquid pharmaceutical composition, e.g., from 0.2% w/v to 0.7% w/v, from 0.2% w/v to 0.65% w/v, from 0.2% w/v to 0.6% w/v, from 0.2% w/v to 0.55% w/v, or from 0.2% w/v to 0.5% w/v. In certain embodiments, the amount of xanthan gum used provides from 0.2% w/v to 0.75% w/v xanthan gum in the final liquid pharmaceutical composition, e.g., from 0.2% w/v to 0.7% w/v, from 0.2% w/v to 0.6% w/v, from 0.25% w/v to 0.75% w/v, from 0.25% w/v to 0.7% w/v, or from 0.25% w/v to 0.6% w/v.

In certain embodiments, the wetting agent is selected from glycols, glycol ether, glycerin, polyoxyethylene alcohols, polyoxyethylene fatty acid esters, and combinations thereof. In certain embodiments, the wetting agent comprises glycerin. In certain embodiments, the wetting agent consists of glycerin. The amount of wetting agent used in the methods can be any suitable amount, including amounts that would achieve the amounts described hereinabove for the compositions. In certain embodiments, the amount of wetting agent used provides from 1% w/v to 30% w/v in the final liquid pharmaceutical composition, e.g., from 10% to 20% w/v. In certain embodiments, the wetting agent is glycerin and is used in an amount that provides from 1% w/v to 30% w/v glycerin in the final liquid pharmaceutical composition, e.g., the liquid pharmaceutical composition obtained at step (c), e.g., from 10% to 20% w/v.

In certain embodiments of preparing the dispersion (e.g., step (a)), the total amount of the wetting agent in the final liquid pharmaceutical composition is used to prepare the dispersion, e.g., is added to the first vessel of step (a) to prepare the dispersion, e.g., in one aliquot. In other embodiments, only a portion of the total amount of wetting agent being used (e.g., a majority portion thereof as illustrated below) is used to prepare the dispersion, and a second portion (e.g., a minority portion of the total amount of wetting agent being used) is used for rinsing, to maximize the amount of dispersion added to the mixture of water and at least one water-soluble excipient. Thus, for example, in some embodiments of step (a), the total amount of wetting agent in the final liquid pharmaceutical composition is added to the first vessel in one or more portions, e.g., two portions. In such embodiments, a first portion of the wetting agent (e.g., a majority amount of the total amount) is used to prepare the dispersion and a second portion of the wetting agent (e.g., a minority amount of the total amount being used, e.g., the amount remaining after preparation of the dispersion) is used for rinsing the first vessel following addition of the dispersion to the mixture (e.g., following step (c)). In certain embodiments, a majority of the total amount of wetting agent is used to prepare the dispersion, e.g., is added to the first vessel as one portion, e.g., at least 75% of the total amount of wetting agent in the final liquid pharmaceutical composition is added to the first vessel, including at least 80%, at least 85%, at least 90%, at least 95%, or at least 97%.

In certain embodiments of preparing the dispersion (e.g., step (a)), the dispersion is prepared in a vessel configured for mixing, e.g., the first vessel is configured mixing, e.g., conventional mixing. In certain embodiments of preparing the dispersion (e.g., step (a)), the dispersion is prepared in a vessel configured for low shear mixing, e.g., with one or more propeller mixers. In certain embodiments of preparing the dispersion (e.g., step (a)), the dispersion is prepared in a vessel configured for high shear mixing, e.g., the first vessel is configured for high shear mixing. In certain embodiments of preparing the dispersion (e.g., step (a)), the dispersion is prepared in a vessel configured for high shear mixing, e.g., the first vessel is equipped with two or more propeller mixing blades, wherein the first propeller mixing blade and second propeller mixing blade are suitably spaced apart to promote sufficient dispersion. The dimensions and relative spacing of the propeller mixing blades used for preparing the dispersion (e.g., in step (a)) can be any suitable dimensions effective to achieve suitable mixing of the components in the vessel and may depend on the size of the vessel and/or the amount of composition being formulated.

In certain embodiments of preparing the dispersion (e.g., step (a)), the two propeller mixing blades are from 6 to 24 inches in diameter, e.g., from 6 to 20 inches, from 6 to 16 inches, from 6 to 12 inches, from 12 to 24 inches, from 12 to 20 inches, from 16 to 24 inches, from 16 to 20 inches, or from 20 to 24 inches. The two propeller mixing blades are affixed on a shaft that can be from 50 to 80 inches in length, e.g., from 50 to 70 inches, from 50 to 60 inches, from 60 to 80 inches, from 60 to 70 inches, or from 70 to 80 inches. In certain embodiments, the shaft is 62 inches in length. In certain embodiments, two 6-to-24-inch diameter propeller mixing blades are positioned along a 50-to-80-inch shaft. In certain embodiments, two 12-inch diameter propeller mixing blades are positioned along a 62-inch-long shaft.

In certain embodiments of preparing the dispersion (e.g., step (a)), the second propeller is positioned above the first propeller at a spacing that promotes sufficient mixing. In certain embodiments, the second propeller is positioned at least 2 inches above the first propeller, e.g., at least 4 inches, at least 6 inches, at least 8 inches, at least 10 inches, at least 12 inches, at least 14 inches, at least 16 inches, at least 18 inches, or at least 20 inches. In certain embodiments, the second propeller is positioned from 2 to 20 inches above the first propeller, e.g., from 6 to 20 inches or from 10 to 20 inches. In certain embodiments, the second propeller is positioned 12 inches above the first propeller.

In certain embodiments of preparing the dispersion (e.g., step (a)), the wetting agent (or majority portion thereof as discussed above) is added first, followed by addition of the at least one suspending agent, then addition of celecoxib. In certain embodiments, the at least one suspending agent is mixed to disperse prior to addition of celecoxib. In certain embodiments, following addition of the wetting agent (or majority portion thereof), xanthan gum is added and mixed to disperse; then synthetic magnesium aluminometasilicate is added and mixed to disperse; and then celecoxib is added and mixed to disperse.

In certain embodiments of preparing the dispersion (e.g., step (a)), the contents of the dispersion (e.g., in first vessel) are mixed, e.g., with conventional mixing such as a blender. In certain embodiments of preparing the dispersion (e.g., step (a)), the contents of the dispersion (e.g., in first vessel) are mixed with low shear e.g., using propellers as described above. In certain embodiments of preparing the dispersion (e.g., step (a)), the contents of the dispersion (e.g., in first vessel) are mixed with high shear, e.g., using propellers as described above. In certain embodiments, high shear mixing is used to mix and disperse the celecoxib in the wetting agent. In certain embodiments, high shear mixing is used to mix and disperse the suspending agents in the wetting agent. In certain embodiments, high shear mixing is used during addition of the suspending agents. In certain embodiments, high shear mixing is used during addition of the celecoxib.

In certain embodiments of preparing the mixture comprising water and suspending agent(s) (e.g., step (b)), the total amount of water in the final liquid pharmaceutical composition is used to prepare the mixture (e.g., is added to the second vessel of step (b) to prepare the mixture, e.g., in one aliquot). In other embodiments, only a portion of the total amount of water being used (e.g., a majority portion thereof as illustrated below) is used to prepare the mixture, and a second portion (e.g., a minority portion of the total amount of water being used) is added after the dispersion is added to the mixture (e.g., after step (c)) to achieve the target final water content of the liquid pharmaceutical composition. Thus, in certain embodiments of step (b), the total amount of water in the final liquid pharmaceutical composition is added to the second vessel in one or more portions, e.g., two portions. In such embodiments, a first portion of the water (e.g., a majority amount of the total amount) is used to prepare the mixture and a second portion of water (e.g., a minority amount of the total amount of water being used, e.g., the portion remaining after preparation of the mixture) is added to the second vessel after step (c) to achieve the target final water content of the liquid pharmaceutical composition. In certain embodiments, a majority portion of the total amount water is used to prepare the mixture, e.g., is added to the second vessel in step (b), e.g., at least 75% of the total amount of water in the final liquid pharmaceutical composition is used to prepare the mixture (e.g., is added to the second vessel in step (b)), including at least 80%, at least 85%, at least 90%, at least 95%, or at least 97%. The amount of water used in the methods can be any suitable amount, including those described hereinabove for the compositions. In certain embodiments, the total amount of water used provides a water content of the final liquid pharmaceutical composition e.g., the liquid pharmaceutical composition obtained at step (c), of from 50% w/v to 95% w/v, e.g., from 80% w/v to 90% w/v.

In certain embodiments of preparing the mixture comprising water and suspending agent(s) (e.g., step (b)), the water is heated prior to addition of the at least one water-soluble excipient to promote dissolution of the excipient(s). This may be particularly relevant to promote dissolution of any preservatives being used. In certain embodiments of step (b), the water is heated to a temperature from 50° C. to 100° C., e.g., from 50° C. to 90° C., from 50° C. to 80° C., from 50° C. to 70° C., from 50° C. to 60° C., from 60° C. to 100° C., from 60° C. to 90° C., from 60° C. to 80° C., from 60° C. to 70° C., from 70° C. to 100° C., from 70° C. to 90° C., from 70° C. to 80° C., from 80° C. to 100° C., from 80° C. to 90° C., or from 90° C. to 100° C. In certain embodiments, the water is heated to a temperature from 70° C. to 80° C.

In certain embodiments of preparing the mixture comprising water and suspending agent(s) (e.g., step (b)), the at least one water-soluble excipient includes at least one preservative, at least one sweetening agent, at least one buffering agent, or a combination thereof. The amounts of preservative, sweetening agent, and buffering agent used in the methods can be any suitable amounts, including amounts that would achieve, in the final liquid pharmaceutical composition e.g., the liquid pharmaceutical composition obtained at step (c), the amounts described hereinabove for the compositions. In certain embodiments, an amount to achieve from 0.001% to 5% w/v of at least one preservative is added, e.g., an amount to achieve from 0.05% w/v to 0.5% w/v. In certain embodiments, an amount to achieve an amount to achieve from 0.001% to 5% w/v of a mixture of methyl paraben and propyl paraben is added, e.g., an amount to achieve from 0.05% w/v to 0.5% w/v. In certain embodiments, an amount to achieve from 0.001% w/v to 5% w/v of at least one high potency sweetener is added, e.g., an amount to achieve from 0.05% w/v to 0.5% w/v. In certain embodiments, an amount to achieve from 0.001% w/v to 5% w/v of sucralose is added, e.g., an amount to achieve from 0.05% w/v to 0.5% w/v. In certain embodiments, an amount to achieve from 0.001% w/v to 5% w/v of at least one buffering agent is added, e.g., an amount to achieve from 0.1% w/v to 2% w/v. In certain embodiments, an amount to achieve from 0.001% w/v to 5% w/v of a mixture of citric acid and sodium citrate dihydrate is added, e.g., an amount to achieve from 0.1% w/v to 2% w/v, from 0.1% w/v to 1.5% w/v, from 0.1% w/v to 1% w/v, or from 0.1% w/v to 0.5% w/v.

In certain embodiments of preparing the mixture comprising water and suspending agent(s) (e.g. step (b)), the water is heated prior to addition of a preservative (e.g., to a temperature from 70° C. to 80° C.), and a preservative is added to the heated water and mixed to dissolve. In certain embodiments, the preservative comprises methyl paraben and propyl paraben, e.g., in certain embodiments, methyl paraben and propyl paraben are added to heated water (e.g., water heated to a temperature from 70° C. to 80° C.) and mixed to dissolve.

In certain embodiments of preparing the mixture comprising water and suspending agent(s) (e.g., step (b)), following addition of the at least one preservative and mixing to dissolve, the mixture is cooled to room temperature prior to addition of any remaining water-soluble excipients. In certain embodiments, following addition of the at least one preservative and mixing to dissolve, the heated temperature is maintained while the remaining water-soluble excipients are added. In certain embodiments, mixing is performed with addition of each excipient and continued to achieve dissolution of the excipient prior to addition of a further excipient. Once dissolution of a first excipient is observed, the next excipient is added to the mixture. In certain embodiments, the at least one preservative (e.g., methyl paraben and propyl paraben) are added first, then the at least one buffering agent (e.g., citric acid and sodium citrate), and then the at least one sweetening agent (e.g., sucralose).

In certain embodiments of preparing the mixture comprising water and suspending agent(s) (e.g., step (b)), the contents of the mixture (e.g., in the second vessel of step (b)) are mixed. In certain embodiments of preparing the mixture comprising water and suspending agent(s) (e.g., step (b)), the contents of the mixture (e.g., in the second vessel of step (b)) are mixed with low shear. In certain embodiments of preparing the mixture comprising water and suspending agent(s) (e.g., step (b)), the contents of the mixture (e.g., in the second vessel of step (b)) are mixed with high shear. In certain embodiments, high shear mixing is used to mix and dissolve at least one water-soluble excipient. In certain embodiments, high shear mixing is used to mix and dissolve the at least one buffering agent. In certain embodiments, high shear mixing is used to mix and dissolve the at least one sweetening agent. In certain embodiments, high shear mixing is used during addition of at least one water-soluble excipient. In certain embodiments, high shear mixing is used during addition of all water-soluble excipients. In certain embodiments, high shear mixing is not used when the at least one preservative is added.

In certain embodiments of adding the dispersion to the mixture comprising water and at least one water-soluble excipient (e.g., step (c)), following addition of the dispersion (e.g., of the first vessel of step (a)) to the mixture (e.g., the second vessel of step (b)), the resulting mixture (e.g., the contents of the second vessel in step (c)) are mixed. In certain embodiments of adding the dispersion to the mixture comprising water and at least one water-soluble excipient (e.g., step (c)), following addition of the dispersion (e.g., of the first vessel of step (a)) to the mixture (e.g., the second vessel of step (b)), the resulting mixture (e.g., the contents of the second vessel in step (c)) are mixed with low shear. In certain embodiments of adding the dispersion to the mixture comprising water and at least one water-soluble excipient (e.g., step (c)), following addition of the dispersion (e.g., of the first vessel of step (a)) to the mixture (e.g., the second vessel of step (b)), the resulting mixture (e.g., the contents of the second vessel in step (c)) are mixed with high shear. In certain embodiments, high shear mixing is used during addition of the dispersion to the mixture, e.g., during addition of the dispersion of the first vessel to the second vessel.

In certain embodiments of adding the dispersion to the mixture comprising water and at least one water-soluble excipient (e.g., step (c), following addition of the dispersion to the mixture (e.g., following addition of the dispersion of the first vessel to the second vessel), a remaining portion of wetting agent is used for rinsing and the rinsing contents are added to the final mixture, e.g., the first vessel is rinsed with a remaining portion of wetting agent and the contents are added to the second vessel.

In certain embodiments, the method further comprises adjusting the pH of the liquid pharmaceutical composition to achieve a target pH. The target pH may be any suitable pH as discussed above for the compositions. In certain embodiments, the target pH is from 3 to 9, including from 4 to 6 or from 4.5 to 5.5. In certain embodiments, sodium hydroxide and hydrochloric acid are used as needed to achieve the target pH.

In certain embodiments, the method further comprises, following addition of the dispersion to the mixture (e.g. following addition of the dispersion of the first vessel to the second vessel in step (c)), adding water (e.g., further portions of the total amount of water being used) as needed to achieve the target final water content of a final liquid pharmaceutical composition.

In certain embodiments, a powder/liquid homogenizer is used during one or more of the above mixing and dispersion steps.

4. Methods of Use

In another aspect, the present disclosure provides a method of administering celecoxib comprising orally administering a liquid pharmaceutical composition as described herein.

In another aspect, the present disclosure provides a method of treating a disease or disorder in a subject in need thereof, the method comprising orally administering to the subject a therapeutically effective amount of a liquid pharmaceutical composition described herein.

In certain embodiments, the disease or disorder is one or more selected from osteoarthritis, rheumatoid arthritis, juvenile rheumatoid arthritis, ankylosing spondylitis, acute pain, and primary dysmenorrhea. In certain embodiments, the disease or disorder is one or more selected from osteoarthritis, rheumatoid arthritis, juvenile rheumatoid arthritis, and ankylosing spondylitis.

In certain embodiments, the subject is a human. In certain embodiments, e.g., wherein the disease or disorder is juvenile rheumatoid arthritis, the human subject is 16 years old or less. In certain embodiments, e.g., wherein the disease or disorder is osteoarthritis, the human subject is 65 years old or more.

In certain embodiments, a dose of the liquid pharmaceutical composition comprising from 50 mg to 1,000 mg celecoxib is administered orally to the subject, e.g., a dose comprising from 50 mg to 900 mg, from 50 mg to 800 mg, from 50 mg to 700 mg, from 50 mg to 600 mg, from 50 mg to 500 mg, from 50 mg to 400 mg, from 50 mg to 300 mg, from 50 mg to 200 mg, or from 50 mg to 100 mg. In certain embodiments, a dose of the liquid pharmaceutical composition comprising from 50 mg to 200 mg celecoxib is administered orally to the subject, e.g., a dose comprising from 50 mg to 175 mg, from 50 mg to 150 mg, from 50 mg to 125 mg, from 50 mg to 100 mg, from 50 mg to 75 mg, from 75 mg to 200 mg, from 75 mg to 175 mg, from 75 mg to 150 mg, from 75 mg to 125 mg, from 75 mg to 100 mg, from 100 mg to 200 mg, from 100 mg to 175 mg, from 100 mg to 150 mg, from 100 mg to 125 mg, from 125 mg to 200 mg, from 125 mg to 175 mg, from 125 mg to 150 mg, from 150 mg to 200 mg, from 150 mg to 175 mg, or from 175 mg to 200 mg.

In certain embodiments, a dose of the liquid pharmaceutical composition comprising 50 mg celecoxib is administered orally to the subject. In certain embodiments, a dose of the liquid pharmaceutical composition comprising 100 mg celecoxib is administered orally to the subject. In certain embodiments, a dose of the liquid pharmaceutical composition comprising 200 mg celecoxib is administered orally to the subject. In certain embodiments, a dose of the liquid pharmaceutical composition comprising 300 mg celecoxib is administered orally to the subject. In certain embodiments, a dose of the liquid pharmaceutical composition comprising 400 mg celecoxib is administered orally to the subject.

In certain embodiments, a dose of the liquid pharmaceutical composition comprises a volume from 1 mL to 50 mL, e.g., from 1 mL to 40 mL, from 1 mL to 30 mL, from 1 mL to 20 mL, from 1 mL to 10 mL, from 10 mL to 50 mL, from 20 mL to 50 mL, from 20 mL to 40 mL, from 20 mL to 30 mL, from 30 mL to 50 mL, from 30 mL to 40 mL, or from 40 mL to 50 mL. In certain embodiments, a dose of the liquid pharmaceutical composition comprises a volume from 15 mL to 25 mL, e.g., 20 mL. In certain embodiments, a dose of the liquid pharmaceutical composition is administered orally to the subject once per day. In certain embodiments, a dose of the liquid pharmaceutical composition is administered orally to the subject twice per day. In certain embodiments, a dose of the liquid pharmaceutical composition is administered orally to the subject three or more times per day.

In certain embodiments, a dose of the liquid pharmaceutical composition comprising 50 mg celecoxib is administered orally to the subject twice daily. In certain embodiments, a dose of the liquid pharmaceutical composition comprising 100 mg celecoxib is administered orally to the subject once daily. In certain embodiments, a dose of the liquid pharmaceutical composition comprising 100 mg celecoxib is administered orally to the subject twice daily. In certain embodiments, a dose of the liquid pharmaceutical composition comprising 200 mg celecoxib is administered orally to the subject once daily. In certain embodiments, a dose of the liquid pharmaceutical composition comprising 200 mg celecoxib is administered orally to the subject twice daily. In certain embodiments, a dose of the liquid pharmaceutical composition comprising 400 mg celecoxib is administered orally to the subject once daily. In certain embodiments, a dose of the liquid pharmaceutical composition comprising 400 mg celecoxib is administered orally to the subject twice daily.

In certain embodiments, the liquid pharmaceutical composition is administered orally to the subject under fed conditions.

5. Methods of Determining Dissolution Profile

In another aspect, the present disclosure provides a method for determining the dissolution profile of a liquid pharmaceutical composition comprising celecoxib. In certain embodiments, the method comprises:

(a) providing a first vessel comprising a dissolution medium, e.g., comprising 0.04M sodium phosphate tribasic and 0.5% w/v sodium dodecyl sulfate (SDS) having a pH of 11.1, wherein the dissolution medium at a temperature of 37° C. and optionally is agitated;

(b) adding the liquid pharmaceutical composition to the first vessel and agitating;

(c) obtaining samples from the first vessel at three or more time points from 5 minutes to 90 minutes after adding the liquid pharmaceutical composition to the first vessel; and (d) determining the quantity of dissolved celecoxib in each sample.

The liquid pharmaceutical composition may be a suspension, e.g., a suspension formulation described hereinabove.

In certain embodiments, the contents of the first vessel. e.g., the dissolution medium and liquid pharmaceutical composition, is agitated with a paddle apparatus. In certain embodiments, the dissolution medium is agitated with a paddle apparatus having a paddle speed from 50 rpm to 100 rpm, e.g., 75 rpm.

In certain embodiments, from 10 mL to 50 mL of the liquid pharmaceutical composition is added to the first vessel in step (b), e.g., from 10 mL to 40 mL, from 10 mL to 30 mL, from 10 mL to 20 mL, from 20 mL to 50 mL, from 20 mL to 40 mL, from 20 mL to 30 mL, from 30 mL to 50 mL, from 30 mL to 40 mL, or from 40 mL to 50 mL. In certain embodiments, 20 mL of the liquid pharmaceutical composition is added to the first vessel in step (b).

In certain embodiments, the liquid pharmaceutical composition is added to the first vessel via a second vessel. In certain embodiments, the second vessel is rinsed with an aliquot of fresh dissolution medium, and the contents are added to the first vessel.

In certain embodiments, the liquid pharmaceutical composition is added to the first vessel over 20 to 30 seconds.

In certain embodiments, the time points of step (c) are selected from 5, 10, 15, 20, 30, 45, 60, and 90 minutes after addition of the liquid pharmaceutical composition to the first vessel. In certain embodiments, the time points of step (c) are 15, 30, and 45 minutes after addition of the liquid pharmaceutical composition to the first vessel.

In certain embodiments, the method further comprises filtering each sample obtained in step (c) prior to determining the quantity of dissolved celecoxib therein in step (d).

The present disclosure will be understood more readily by reference to the following examples, which are provided by way of illustration only and are not intended to be limiting.

6. Embodiments

Embodiment 1. A liquid pharmaceutical composition comprising celecoxib, suspending agents comprising xanthan gum and from 0.05% w/v to 2% w/v of a synthetic magnesium aluminometasilicate, and a liquid carrier.

Embodiment 2. The liquid pharmaceutical composition of embodiment 1, wherein the concentration of celecoxib is from 0.1 mg/mL to 100 mg/mL.

Embodiment 3. The liquid pharmaceutical composition of embodiment 1, wherein the concentration of celecoxib is from 1 mg/mL to 20 mg/mL.

Embodiment 4. The liquid pharmaceutical composition of embodiment 1, wherein the concentration of celecoxib is from 5 mg/mL to 15 mg/mL.

Embodiment 5. The liquid pharmaceutical composition of embodiment 1, wherein the concentration of celecoxib is 10 mg/mL.

Embodiment 6. The liquid pharmaceutical composition of any one of embodiments 1-5, wherein the celecoxib is celecoxib polymorphic Form III.

Embodiment 7. The liquid pharmaceutical composition of any one of embodiments 1-6 in the form of a suspension.

Embodiment 8. The liquid pharmaceutical composition of embodiment 7, wherein the suspension comprises celecoxib-containing particles having a particle size distribution with a D10 of from 1 to 5 μm, a D50 from 8 to 12 μm, and a D90 from 20 to 26 μm.

Embodiment 9. The liquid pharmaceutical composition of embodiment 7, wherein the suspension comprises celecoxib-containing particles having a particle size distribution with a D10 of not less than (NLT) 1 μm, a D50 from 5 to 12.5 μm, and a D90 of not more than (NMT) 30 μm.

Embodiment 10. The liquid pharmaceutical composition of any one of embodiments 1-9, wherein the suspending agents consist essentially of a mixture of xanthan gum and from 0.1% w/v to 0.75% w/v of a synthetic magnesium aluminometasilicate.

Embodiment 11. The liquid pharmaceutical composition of any one of embodiments 1-10, wherein the weight ratio of xanthan gum to synthetic magnesium aluminometasilicate is from 2:1 to 1:2.

Embodiment 12. The liquid pharmaceutical composition of any one of embodiments 1-10, wherein the weight ratio of xanthan gum to synthetic magnesium aluminometasilicate is 1:1.

Embodiment 13. The liquid pharmaceutical composition of any one of embodiments 1-12, wherein the xanthan gum is present in an amount from 0.2% w/v to 2% w/v of the composition.

Embodiment 14. The liquid pharmaceutical composition of any one of embodiments 1-12, wherein the xanthan gum is present in an amount from 0.25% w/v to 0.75% w/v of the composition.

Embodiment 15. The liquid pharmaceutical composition of any one of embodiments 1-12, wherein the xanthan gum is present in an amount of 0.5% w/v of the composition.

Embodiment 16. The liquid pharmaceutical composition of any one of embodiments 1-15, wherein the synthetic magnesium aluminometasilicate is present in an amount from 0.2% w/v to 0.6% w/v of the composition.

Embodiment 17. The liquid pharmaceutical composition of any one of embodiments 1-15, wherein the synthetic magnesium aluminometasilicate is present in an amount of 0.5% w/v of the composition.

Embodiment 18. The liquid pharmaceutical composition of any one of embodiments 1-17, wherein the synthetic magnesium aluminometasilicate is amorphous.

Embodiment 19. The liquid pharmaceutical composition of embodiment 18, wherein the synthetic magnesium aluminometasilicate has a loose bulk density from 0.06 to 0.11 g/mL.

Embodiment 20. The liquid pharmaceutical composition of embodiment 18 or 19, wherein the synthetic magnesium aluminometasilicate has a tapped bulk density from 0.1 to 0.17 g/mL.

Embodiment 21. The liquid pharmaceutical composition of any one of embodiments 18-20, wherein the synthetic magnesium aluminometasilicate has an average particle size of 3.1 μm.

Embodiment 22. The liquid pharmaceutical composition of any one of embodiments 1-21, further comprising one or more pharmaceutically acceptable excipients selected from preservatives, sweetening agents, buffering agents, coloring agents, flavoring agents, and pH modifiers.

Embodiment 23. The liquid pharmaceutical composition of embodiment 22, wherein the preservative is present in an amount from 0.001% w/v to 5% w/v, e.g., from 0.01% w/v to 1% w/v or from 0.05% w/v to 0.5% w/v of the composition.

Embodiment 24. The liquid pharmaceutical composition of embodiment 22 or 23, wherein the preservative is selected from benzyl alcohol, methyl paraben, propyl paraben, butyl paraben, ethyl paraben, sorbic acid, potassium sorbate, benzalkonium chloride, benzoic acid, sodium benzoate, and combinations thereof.

Embodiment 25. The liquid pharmaceutical composition of embodiment 23 or 24, wherein the preservative comprises methyl paraben and propyl paraben.

Embodiment 26. The liquid pharmaceutical composition of embodiment 22, wherein the buffering agent is present in an amount from 0.001% w/v to 5% w/v, e.g., from 0.1% w/v to 2% w/v or from 0.1% w/v to 1.5% w/v of the composition.

Embodiment 27. The liquid pharmaceutical composition of embodiment 22 or 26, wherein the buffering agent is selected from citric acid, sodium citrate dihydrate, citric acid monohydrate, phosphoric acid, succinic acid, tartaric acid, lactic acid, acetic acid and salts thereof, sodium hydroxide, sodium phosphate, disodium hydrogen phosphate, sodium hydrogen carbonate, monosodium phosphate, monopotassium phosphate, dipotassium phosphate, potassium citrate, gluconic acid and salts thereof, and combinations thereof.

Embodiment 28. The liquid pharmaceutical composition of embodiment 22 or 27, wherein the buffering agent comprises citric acid and sodium citrate dihydrate.

Embodiment 29. The liquid pharmaceutical composition of embodiment 22, wherein the sweetening agent comprises a high potency sweetener, wherein the high potency sweetener is present in an amount from 0.001% w/v to 5% w/v of the composition, e.g., from 0.01% w/v to 1% w/v or from 0.05% w/v to 0.5% w/v.

Embodiment 30. The liquid pharmaceutical composition of embodiment 29, wherein the high potency sweetener is selected from sodium saccharin, potassium saccharin, sodium cyclamate, aspartame, thaumatin, acesulfame potassium, sucralose, alitame, neotame, xylose, ribose, mannose, galactose, neohesperidin dihydrochalcone, stevia, monk fruit, and combinations thereof.

Embodiment 31. The liquid pharmaceutical composition of embodiment 29, wherein the high potency sweetener is sucralose.

Embodiment 32. The liquid pharmaceutical composition of embodiment 22, wherein the pH modifier comprises sodium hydroxide, hydrochloric acid, or a combination thereof.

Embodiment 33. The liquid pharmaceutical composition of any one of embodiments 1-32, wherein the liquid carrier comprises water and a wetting agent.

Embodiment 34. The liquid pharmaceutical composition of embodiment 33, wherein water is present in an amount from 50% w/v to 95% w/v of the composition, e.g., from 75% w/v to 95% w/v, or from 80% w/v to 95% w/v.

Embodiment 35. The liquid pharmaceutical composition of embodiment 33 or 34, wherein the wetting agent is present in an amount from 1% w/v to 30% w/v of the composition, e.g., from 1% w/v to 20% w/v or from 10% w/v to 20% w/v.

Embodiment 36. The liquid pharmaceutical composition of embodiment 33 or 35, wherein the wetting agent is selected from glycols, glycol ether, glycerin, polyoxyethylene alcohols, polyoxyethylene fatty acid esters, and combinations thereof.

Embodiment 37. The liquid pharmaceutical composition of embodiment 35 or 36, wherein the wetting agent comprises glycerin.

Embodiment 38. The liquid pharmaceutical composition of embodiment 1 comprising:

from 0.01 mg/mL to 100 mg/mL celecoxib; suspending agents comprising from 0.2% w/v to 2% w/v xanthan gum and from 0.05% w/v to 2% w/v of a synthetic magnesium aluminometasilicate; from 0.001% w/v to 5% w/v of a preservative; from 0.001% w/v to 5% w/v of a buffering agent; from 0.001% w/v to 5% w/v of a sweetening agent; and a liquid carrier comprising from 50% w/v to 95% w/v water and from 1% w/v to 30% w/v of a wetting agent.

Embodiment 39. The liquid pharmaceutical composition of embodiment 1 comprising:

from 1 mg/mL to 20 mg/mL celecoxib; suspending agents comprising from 0.25% w/v to 0.75% w/v xanthan gum and from 0.2% w/v to 0.6% w/v of a synthetic magnesium aluminometasilicate; from 0.01% w/v to 1% w/v of a preservative; from 0.1% w/v to 2% w/v of a buffering agent; from 0.01% w/v to 1% w/v of a sweetening agent; and a liquid carrier comprising from 80% w/v to 95% w/v water and from 1% w/v to 20% w/v of a wetting agent.

Embodiment 40. The liquid pharmaceutical composition of embodiment 1 comprising:

10 mg/mL celecoxib; suspending agents comprising 0.5% w/v xanthan gum and 0.5% w/v of a synthetic magnesium aluminometasilicate; from 0.05% w/v to 0.5% w/v of a preservative; from 0.1% w/v to 2% w/v of a buffering agent; from 0.05% w/v to 0.5% w/v of a sweetening agent; and a liquid carrier comprising from 80% w/v to 90% w/v water and from 10% w/v to 20% w/v of a wetting agent.

Embodiment 41. The liquid pharmaceutical composition of any one of embodiments 38-40, wherein: the preservative comprises methyl paraben and propyl paraben, the buffering agent comprises citric acid and sodium citrate dihydrate, the sweetening agent comprises sucralose, and the liquid carrier comprises water and glycerin.

Embodiment 42. The liquid pharmaceutical composition of any one of the preceding embodiments, wherein the composition does not comprise sodium lauryl sulfate.

Embodiment 43. The liquid pharmaceutical composition of any one of the preceding embodiments, wherein the composition has a pH from 3 to 9.

Embodiment 44. The liquid pharmaceutical composition of embodiment 43, wherein the composition has a pH above 5.2.

Embodiment 45. The liquid pharmaceutical composition of any one of the preceding embodiments, wherein the pH of the composition does not change by more than 0.5 following storage for one month at 25° C.

Embodiment 46. The liquid pharmaceutical composition of any one of the preceding embodiments, wherein the composition does not include one or more or all of sodium lauryl sulfate, propylene glycol, and purified (natural) magnesium aluminum silicate.

Embodiment 47. The liquid pharmaceutical composition of any one of the preceding embodiments, wherein the composition is in the form of a suspension and exhibits one or both of (i) a uniformity difference in celecoxib content between the top of the composition and the bottom of the composition of less than 5% following storage in a closed bottle at 25° C. in an upright orientation for six months and (ii) a uniformity difference in celecoxib content between the top of the composition and the bottom of the composition of less than 5% following storage in a closed bottle at 40° C. in an upright orientation for six months, wherein the composition is shaken for 30 seconds prior to measuring celecoxib content.

Embodiment 48. The liquid pharmaceutical composition of any one of the preceding embodiments, wherein when the composition is subjected to Dissolution Test Conditions, the composition exhibits a celecoxib release profile characterized by: (a) from 5% to 45% celecoxib release in 5 minutes, (b) from 15% to 50% celecoxib release in 10 minutes, (c) from 30% to 75% celecoxib release in 15 minutes, (d) from 55% to 85% celecoxib release in 20 minutes, and (e) greater than 80% celecoxib release in 30 minutes

| Dissolution Test Conditions | |
|---|---|
| Media | 0.04M Sodium Phosphate Tribasic, pH adjusted to 11.1 with $H_3PO_4$, with a sodium dodecyl sulfate (SDS) concentration of 0.5% |
| Media Volume | 1000 mL |
| Paddle Speed | 75 rpm |
| Media Temperature | 37° C. |

Embodiment 49. The liquid pharmaceutical composition of embodiment 48, wherein the composition exhibits a celecoxib release profile characterized by: (a) from 5% to 25% celecoxib release in 5 minutes, (b) from 26% to 35% celecoxib release in 10 minutes, (c) from 40% to 60% celecoxib release in 15 minutes, (d) from 62% to 80% celecoxib release in 20 minutes, and (e) greater than 85% celecoxib release in 30 minutes.

Embodiment 50. The liquid pharmaceutical composition of any one of the preceding embodiments, wherein the composition is bioequivalent to a corresponding dose of CELEBREX® (celecoxib) capsules, when assessed by oral administration.

Embodiment 51. The liquid pharmaceutical composition of embodiment 50, wherein the composition is a suspension according to Table A:

TABLE A

| Ingredient | Amount (% w/v) |
|---|---|
| Celecoxib | 1 |
| Xanthan Gum | 0.5 |
| Synthetic Magnesium Aluminometasilicate | 0.5 |
| Citric Acid Anhydrous | 0.7 |
| Sodium Citrate Dihydrate | 1.1 |
| Methylparaben | 0.15 |
| Propylparaben | 0.05 |
| Sucralose | 0.1 |
| Glycerin | 15.0 |
| Purified Water | QS |
| Total | 100% |

Embodiment 52. The liquid pharmaceutical composition of any one of the preceding embodiments, in the form of a suspension according to Table A above, wherein oral administration to a subject of a dose of the liquid pharmaceutical composition comprising from 200 mg celecoxib is bioequivalent to oral administration of a capsule containing 200 mg celecoxib in a formulation having the components of Table B below:

TABLE B

| Ingredient |
|---|
| Celecoxib |
| Croscarmellose sodium |
| Edible inks |
| Gelatin |
| Lactose monohydrate |
| Magnesium stearate |
| Povidone |
| Sodium lauryl sulfate |

Embodiment 53. The liquid pharmaceutical composition of any one of the preceding embodiments, wherein the liquid pharmaceutical composition has an acid neutralizing capacity from 2 to 5 mEq per 200 mg dose, e.g., from 2 to 3 mEq per 200 mg dose.

Embodiment 54. A method of preparing a liquid pharmaceutical composition comprising:

(a) dispersing celecoxib and suspending agents comprising xanthan gum and synthetic magnesium aluminometasilicate in a wetting agent in a first vessel to obtain a dispersion;

(b) mixing water and at least one water-soluble excipient in a second vessel; and (c) adding the dispersion of the first vessel to the second vessel and mixing to obtain the liquid pharmaceutical composition.

Embodiment 55. The method of embodiment 54, wherein the suspending agents consist of xanthan gum and synthetic magnesium aluminometasilicate.

Embodiment 56. The method of embodiment 54 or 55, wherein the wetting agent is glycerin.

Embodiment 57. The method of any one of embodiments 54-56, wherein one or more of (a), (b), and (c) comprises high shear mixing.

Embodiment 58. The method of any one of embodiments 54-57, wherein the first vessel is equipped with a mixer having at least two propeller mixing blades, wherein the first propeller mixing blade and second propeller mixing blade are spaced suitably apart to promote sufficient dispersion.

Embodiment 59. The method of any one of embodiments 54-58, wherein the wetting agent is added to the first vessel first, then the at least one suspending agent is added to the first vessel and mixed to disperse, and then the celecoxib is added to the first vessel and mixed to disperse.

Embodiment 60. The method of any one of embodiments 54-59, wherein the water-soluble excipient is selected from at least one preservative, at least one sweetening agent, at least one buffering agent, and combinations thereof.

Embodiment 61. The method of any one of embodiments 54-60, wherein the water is heated in the second vessel prior to addition of the at least one water-soluble excipients, optionally wherein the water is heated to a temperature from 50° C. to 100° C.

Embodiment 62. The method of embodiment 61, wherein at least one preservative is added to the heated water and mixed to dissolve.

Embodiment 63. The method of any one of embodiments 60-62, wherein the at least one preservative comprises methyl paraben and propyl paraben.

Embodiment 64. The method of any one of embodiments 61-63, further comprising cooling the mixture, e.g., to room temperature, prior to addition of the at least one water-soluble excipients.

Embodiment 65. The method of any one of embodiments 54-64, further comprising adjusting the pH of the liquid pharmaceutical composition to achieve a target pH from 3 to 9.

Embodiment 66. A method of treating a disease or disorder in a subject in need thereof, the method comprising orally administering to the subject a therapeutically effective amount of the liquid pharmaceutical composition of any one of embodiments 1-53.

Embodiment 67. The method of embodiment 66, wherein the disease or disorder is selected from osteoarthritis, rheumatoid arthritis, juvenile rheumatoid arthritis, ankylosing spondylitis, acute pain, and primary dysmenorrhea.

Embodiment 68. A method of administering celecoxib to a subject in need thereof, the method comprising orally administering to the subject a therapeutically effective amount of the liquid pharmaceutical composition of any one of embodiments 1-53.

Embodiment 69. The method of any one of embodiments 66-68, wherein the subject is a human.

Embodiment 70. The method of embodiment 69, wherein the human subject is 16 years old or less.

Embodiment 71. The method of embodiment 69, wherein the human subject is 65 years old or more.

Embodiment 72. The method of any one of embodiments 66-71, wherein a dose of the liquid pharmaceutical composition comprising from 50 mg to 200 mg celecoxib is administered orally to the subject.

Embodiment 73. The method of embodiment 72, wherein the dose is administered orally to the subject once or twice daily.

Embodiment 74. A method for determining the dissolution profile of a liquid pharmaceutical composition comprising celecoxib, the method comprising:

(a) providing a first vessel comprising a dissolution medium comprising 0.04M sodium phosphate tribasic and 0.5% w/v sodium dodecyl sulfate (SDS) having a pH of 11.1, wherein the dissolution medium is agitated and at a temperature of 37° C.;

(b) adding the liquid pharmaceutical composition to the first vessel;

(c) obtaining samples from the first vessel at three or more time points from 5 minutes to 90 minutes after adding the liquid pharmaceutical composition to the first vessel; and (d) determining a quantity of dissolved celecoxib in each sample.

Embodiment 75. The method of embodiment 74, further comprising agitating the dissolution medium in (a) with a paddle apparatus, optionally at a paddle speed of 75 rpm.

Embodiment 76. The method of embodiments 74 or 75, wherein one or more of:

step (b) comprises adding 20 mL of the liquid pharmaceutical composition to the first vessel;

step (b) comprises adding the liquid pharmaceutical composition to the first vessel via a second vessel which, after addition, is rinsed with an aliquot of fresh dissolution medium and added to the first vessel;

step (b) comprises adding the liquid pharmaceutical composition to the first vessel over 20 to 30 seconds;

the method further comprises filtering each sample obtained in step (c) prior to determining the quantity of dissolved celecoxib therein in step (d);

the three time points of step (c) are selected from 5, 10, 15, 20, 30, 45, 60, and 90 minutes after addition of the liquid pharmaceutical composition to the first vessel; and/or the determining of step (d) is performed by HPLC.

7. Examples

Comparative Example 1

An oral suspension formulation was prepared with the components shown in Table 1:

TABLE 1

| Comparative Celecoxib Oral Suspension | | |
|---|---|---|
| Material | % w/v | mg/mL |
| Celecoxib | 1.00 | 10 |
| Xanthan Gum | 0.25 | 2.5 |
| Citric Acid Anhydrous | 0.40 | 4 |
| Sodium Citrate Dihydrate | 1.10 | 11 |
| Grape Flavor | 0.30 | 3 |
| Glycerin | 15.00 | 150 |
| Propylene Glycol | 5.00 | 50 |
| Sucralose | 0.10 | 1 |
| Methylparaben | 0.15 | 1.5 |
| Propylparaben | 0.05 | 0.5 |
| DI Water | (QS) | (QS) |
| Total | 105.00 | 1050 |

An open label, balanced, randomized, two-treatment, two-period, two-sequence, cross-over, single oral dose comparative bioavailability study of the comparative oral suspension of Table 1 with CELEBREX® (Celecoxib) capsules 200 mg (Pfizer, distributed by G.D.Searle LLC Division of Pfizer Inc, NY, NY 10017) in adult, human subjects, under fasting conditions was conducted.

Healthy, adult, human subjects between 18 and 45 years of age (both inclusive) and weighing at least 50 kgs; body mass index between 18.50 and 24.90 kg/height in $m^2$ (both inclusive) who were willing to participate were enrolled. All subjects who met the inclusion and exclusion criteria as described in the protocol were judged eligible for enrollment in this study, based on medical and medication histories, demographic data (including Sex, Age, Body Weight (kg), Height (cm) and BMI [$kg/m^2$]). Vital signs measurements, ECG, chest x-ray, physical examination, breath alcohol analysis, urine drug screening and clinical laboratory tests.

In each period, a total of 24 blood samples (1×5 mL each) were collected as per the following schedule: Pre-dose (0.00 hour) sample within 1 hour prior to drug administration and the others at 0.50, 1.00, 1.50, 2.00, 2.33, 2.67, 3.00, 3.33, 3.67, 4.00, 4.33, 4.67, 5.00, 5.50, 6.00, 8.00, 10.00, 12.00, 16.00, 24.00, 36.00, 48.00 and 72.00 hours post dose into 5 mL K2EDTA vacutainers.

The following pharmacokinetic (pK) parameters were calculated using a "Non-compartmental model" for Treatments T (=test, Table 1) and R (=reference, CELEBREX®): $AUC_{0-t}$, $AUC_{0-inf}$, $T_{max}$, t½ and $K_{el}$. All pharmacokinetic analysis was carried out using Phoenix® WinNonlin® Version 6.3.

Analysis of variance (ANOVA) was estimated at alpha (α) 0.05 on the ln-transformed pK parameters $AUC_{0-t}$ and $AUC_{0-inf}$ using the PROC GLM procedure of SAS® Version 9.4.

The 90% confidence interval was determined for the differences in the averages (arithmetic means) of the ln-transformed data and then the antilog of the obtained confidence limits for celecoxib concentrations were calculated. The comparison of interest is T vs. R, so the ratios were of the form: Test/Reference. Ratio of means was calculated using the least squares mean (LSM) for ln-transformed $AUC_{0-t}$ and $AUC_{0-inf}$.

A summary of the pharmacokinetic and statistical results is provided in Table 2.

TABLE 2

| PK Parameters for Comparative Celecoxib Oral Suspension | | | | | |
|---|---|---|---|---|---|
| Analyte: Celecoxib | $AUC_{0-t}$ (hr*ng/mL) | $AUC_{0-inf}$ (hr*ng/mL) | *$T_{max}$ (hr) | $K_{el}$ (1/hr) | $t_{1/2}$ (hr) |
| Comparative celecoxib oral suspension 10 mg/mL (T) | | | | | |
| N | 12 | 12 | 12 | 12 | 12 |
| Mean | 7392.7464 | 7607.0190 | 1.500 | 0.0946 | 7.4347 |
| CV (%) | 44.7 | 43.3 | 53.5 | 12.6 | 12.2 |
| CELEBREX © (Celecoxib) capsules, 200 mg (R) | | | | | |
| N | 12 | 12 | 12 | 12 | 12 |
| Mean | 6920.9339 | 7100.2872 | 2.330 | 0.0923 | 7.9822 |
| CV (%) | 38.9 | 37.9 | 37.3 | 21.8 | 31.8 |
| 90% Confidence Intervals | | | | | |
| Lower Limit (%) | 87.15 | 88.39 | | | |
| Upper Limit (%) | 127.04 | 126.31 | | | |
| T/R Ratio (%) | 105.22 | 105.66 | | | |
| Power | 0.6271 | 0.6699 | | | |
| ANOVA (p-Value) | | | | | |
| Sequence | 0.1269 | 0.1215 | | | |
| Period | 0.0422 | 0.0452 | | | |
| Treatment | 0.6351 | 0.5884 | | | |

Note:
*indicates - for $T_{max}$ Median has been reported.

Bioequivalence is declared if the T/R ratios of the geometric least squares means for ln-transformed pharmacokinetic parameters $AUC_{0-t}$ and $AUC_{0-inf}$ and their 90% confidence intervals are within 80.00%-125.00% for celecoxib. Neither $AUC_{0-t}$ nor $AUC_{0-inf}$ was within the acceptable confidence interval limits for bioequivalence to CELEBREX®.

Example 2—Oral Suspension Product of the Present Disclosure

An oral suspension of celecoxib in accordance with the present disclosure was prepared with the components set forth in Table 3:

TABLE 3

| Celecoxib Oral Suspension | |
|---|---|
| Substance | % w/v |
| Celecoxib | 1 |
| Xanthan Gum | 0.5 |
| Citric Acid Anhydrous | 0.7 |
| Sodium Citrate Dihydrate | 1.1 |
| Glycerin | 15 |
| Sucralose | 0.1 |
| Synthetic Magnesium Aluminometasilicate | 0.5 |
| Methylparaben | 0.15 |
| Propylparaben | 0.05 |
| DI Water | 85.90 (QS) |
| Total | 105.00* |

*Density 1.05 g/mL

The product was prepared by the following procedure:

Glycerin (97% of total amount) was added to an appropriately sized side vessel (e.g., 1,000 L) equipped with two propeller mixing blades of 12-inch diameter on a 62-inch shaft. One propeller was at the bottom of the shaft, with the second propeller positioned 12 inches above the first propeller. Xanthan gum was then added to the side vessel to disperse. Synthetic magnesium aluminometasilicate was then added to the glycerin/xanthan gum, and mixed to disperse. Celecoxib was then added and mixed to disperse. Use of the second propeller provided effective incorporation of the synthetic magnesium aluminometasilicate and celecoxib powders. Higher speed mixing with a single propeller led to powder settling at the top of the mixture and incomplete incorporation.

In a main vessel large enough to contain the entire batch (e.g., 5,000 L) and equipped with a dedicated mixer with propeller mixing blades, no less than 95% of the total amount of USP purified water (4,080 kg per 5000 L) was added and heated to 75° C. Methyl paraben and propyl paraben were added with heat and mixing to dissolve. The mixture was allowed to cool, then citric acid was added with mixing to dissolve. Sucralose was added with mixing to dissolve, then sodium citrate was added with mixing to dissolve.

The contents of the side vessel were transferred to the main vessel. The side vessel was rinsed with glycerin (the remaining 3% of the total amount) to ensure complete addition. The main vessel was mixed to ensure uniform dispersion.

The pH of the resulting suspension was measured to confirm a target of pH 5. The pH was adjusted, if necessary, with NaOH or HCl to achieve the target pH.

USP purified water was added as needed (QS) to the target final weight. The finished suspension was mixed to ensure complete and uniform dispersion.

In certain embodiments (e.g., the registration batches referred to herein as Lots A-C), a Silverson Flashmix homogenizer with stator (round holes) was used to recirculate and impart high shear mixing during every step of the procedure, except during the heating and mixing to dissolve the parabens.

Example 3—Bioequivalence Study for a Product of the Present Disclosure

This study was an open-label, laboratory-blinded, randomized, single dose, three-period, six-sequence, two-treatment crossover comparative study in healthy male and female adult subjects under fasting and fed conditions. Fifty-four (54) subjects in total were included and dosed.

The primary objectives were to evaluate the pharmacokinetic (pK) profile and to compare the bioavailability of 200 mg Test Product in accordance with the present disclosure (Celecoxib Oral Suspension (10 mg/1 mL)(T) versus Reference Product (CELEBREX® (Celecoxib) Capsules, 200 mg) (R) in healthy adult subjects under fasted conditions and to evaluate the effect of food on the PK profile of Test Product (T) in healthy adult subjects. The Test Product was prepared as described in Example 2, Table 3. Celecoxib exhibits dose-proportional increase in exposure after oral administration up to 200 mg twice daily and less than proportional increase at higher doses. FULL PRESCRIBING INFORMATION, CELEBREX® (celecoxib) capsules, for oral use, Initial U.S. Approval: 1998 (Revised April 2021).

The secondary objective was to evaluate the safety and tolerability of Test Product (T) in healthy subjects under fasted and fed conditions.

The 3-treatment study design (combining $T_{FA}$, $T_{FE}$, $R_{FA}$) was chosen (i) to evaluate the pharmacokinetic (PK) profile and to compare the bioavailability of Test Product (T) versus Reference Product (R) under fasting conditions, and (ii) to evaluate the food effect of the Test Product ($T_{FA}/T_{FE}$ ratio).

$T_{FA}$=Test Product Celecoxib Oral Suspension (10 mg/1 mL), single dose of 20 mL under fasting conditions $T_{FE}$=Test Product Celecoxib Oral Suspension (10 mg/1 mL), single dose of 20 mL under fed conditions $R_{FA}$=Reference Product Celebrex® (celecoxib) Capsules, 200 mg, single dose of one 200 mg capsule under fasting conditions Single oral doses of Celecoxib Oral Suspension (10 mg/1 mL) (T) or Celebrex® (celecoxib) Capsules, 200 mg (R) were administered to subjects under fasting/fed conditions in the morning of Day 1 of each Study Period. Subjects were dosed with a total dose of 600 mg celecoxib using both formulations. Pharmacokinetic parameters for Celecoxib were calculated from plasma concentrations determined by validated HPLC/MS/MS method. A washout period between drug administrations was at least 7 days.

Twenty (21) blood samples were obtained from a forearm vein by an experienced nurse during each Study Period according to the study schedule. Blood collections were made prior to the administration of study product (−1.00) and 0.33, 0.67, 1.00, 1.50, 2.00, 2.50, 3.00, 3.50, 4.00, 4.50, 5.00, 6.00, 8.00, 10.00, 12.00, 14.00, 24.00, 36.00, 48.00 and 72.00 hours after study product administration.

Administration in Study Period 2 and in Study Period 3 followed after a 7-day washout period. All procedures in Study Period 2 and Study Period 3 were identical with Study Period 1 as described above.

Adverse events and clinically significant deviations from laboratory tests, physical examinations and vital signs were reported for the evaluation of safety.

For bioequivalence assessment of Test (T) and Reference (R) Products, pharmacokinetic parameters $AUC_{(0-t)}$ and $AUC_{(0-\infty)}$ of celecoxib were used. For food-effect assessment of the Test Product, the above AUC parameters and the $C_{max}$ of celecoxib were used.

$AUC_{(0-t)}$: Area under the plasma concentration versus time curve calculated by the Linear Up Log Down rule from sampling time zero to sampling time of the last measurable plasma concentration $AUC_{(0-\infty)}$: The area under the plasma concentration-time curve from time zero to infinity.

$C_{max}$: Maximum plasma concentration observed.

Bioequivalence of the test product and the reference product was assessed on the basis of 90% confidence intervals for T/R ratio of LSM for ln-transformed $AUC_{(0-t)}$ and $AUC_{(0-\infty)}$ for celecoxib primary parameters and compared with the standard bioequivalence acceptance range 80.00-125.00% (Tables 4 and 5).

TABLE 4

| Bioequivalence Summary | | | | | | | | | |
|---|---|---|---|---|---|---|---|---|---|
| | GEOMETRIC LEAST SQUARES MEANS | | | | RATIO $T_{FA}/R_{FA}$ | 90% CONFIDENCE LIMITS (%) | | | $CV_{intra}$ |
| Parameter | N | $T_{FA}$ | N | $R_{FA}$. | (%) | Lower | Upper | BE | (%) |
| $AUC_{(0-t)}$ (ng · h/mL) | 51 | 3932.2 | 51 | 4281.5 | 91.84 | 86.79 | 97.19 | YES | 17.15 |
| $AUC_{(0-\infty)}$ (ng · h/mL) | 51 | 4512.7 | 51 | 4784.3 | 94.32 | 89.50 | 99.40 | YES | 15.89 |

N = Number of Observations

The results confirmed that the 90% confidence intervals for Test $T_{FA}$ to Reference $R_{FA}$ ratios of the geometric LSM for $AUC_{(0-t)}$ and $AUC_{(0-\infty)}$ of celecoxib were found within the bioequivalence acceptance range from 80.00% to 125.00%, demonstrating bioequivalence to CELEBREX®.

TABLE 5

| Food Effect Summary | | | | | | | | | |
|---|---|---|---|---|---|---|---|---|---|
| | GEOMETRIC LEAST SQUARES MEANS | | | | RATIO $T_{FE}/T_{FA}$ | 90% CONFIDENCE LIMITS (%) | | Food | $CV_{intra}$ |
| Parameter | N | $T_{FE}$ | N | $T_{FA}$ | (%) | Lower | Upper | Effect | (%) |
| $AUC_{(0-t)}$ (ng · h/mL) | 52 | 5834.9 | 52 | 3899.2 | 149.64 | 139.58 | 160.44 | YES | 21.41 |
| $AUC_{(0-\infty)}$ (ng · h/mL) | 52 | 6048.8 | 52 | 4481.9 | 134.96 | 125.94 | 144.63 | YES | 21.27 |
| $C_{max}$ (ng/ml) | 52 | 791.3 | 52 | 323.8 | 244.36 | 224.42 | 266.08 | YES | 26.33 |

N = Number of Observations

The results of food effect indicate that the extent and rate of absorption of celecoxib was significantly increased when the Test formulation (Celecoxib Oral Suspension (10 mg/1 mL)) was administered under fed conditions compared to the fasting state: a high-fat, high-calorie meal increased the mean $AUC_{(0-t)}$, $AUC_{(0-\infty)}$, and $C_{max}$ of celecoxib by 50%, 35%, and 144%, respectively.

Example 4—Particle Size Distribution Measurements

A target particle size distribution for the celecoxib active pharmaceutical ingredient (API) in a celecoxib oral suspension as described herein is shown in Table 6.

TABLE 6

| API Particle Size Distribution Specification | |
|---|---|
| D10 | NLT 0.5 μm |
| D50 | Between 3-10 μm |
| D90 | NMT 25 μm |

A particle size analysis was performed on the API used in Example 2 per a dry method using a Laser Diffraction Instrument (Sympatec, Helos/KF-Magic F71000 or equivalent) by the manufacturer, PharmaZell (India) (Table 7).

TABLE 7

| Particle Size Distribution, Celecoxib API | | |
|---|---|---|
| Particle Size from Certificate of Analysis | Criteria | Lot PC00017520 |
| D10 | NLT 0.5 | 1 |
| D50 | 3-10 | 5 |
| D90 | NMT 25 | 18 |

The synthetic magnesium aluminometasilicate used in Example 2 was tested by the manufacturer by a method in which the raw material is diluted with water, using a Laser Diffraction Instrument (MICROTRACII Particle-Size Analyzer) (Table 8).

TABLE 8

| Particle Size Distribution, Synthetic Magnesium Aluminometasilicate | | | |
|---|---|---|---|
| Particle Size | Lot 1 | Lot 2 | Lot 3 |
| D10 | 3.14 | 3.16 | 3.11 |
| D50 | 9.29 | 9.19 | 9.11 |
| D90 | 20.81 | 20.65 | 20.95 |

Thus, the particle size distribution results for the celecoxib API and synthetic magnesium aluminometasilicate used to prepare the oral suspension of Example 2 are similar.

A Malvern MasterSizer 3000 instrument and Hydro MV liquid handling unit, with water as the diluent, was used to determine the particle size distribution of particles present in the oral suspension of Example 2. Xanthan gum is water soluble while celecoxib and synthetic magnesium aluminometasilicate are not easily dissolved in water. Thus, particles due to celecoxib and synthetic magnesium aluminometasilicate were analyzed, while xanthan gum did not contribute to the counts.

Registration lots of the celecoxib oral suspension as described in Example 2 (Lots A, B, and C) were evaluated after storage for 12 months at 25° C. and 30° C. Samples stored under accelerated conditions (6 months at 40° C.) were also evaluated. The results are shown in Table 9.

TABLE 9

Particle Size Distribution Data, Stability Testing Through 12 Months

| | Sample | | | | | | | | |
|---|---|---|---|---|---|---|---|---|---|
| | Lot A | Lot B | Lot C | Lot A | Lot B | Lot C | Lot A | Lot B | Lot C |
| | Age/Condition | | | | | | | | |
| | 6 mo./ 40° C. | 6 mo./ 40° C. | 6 mo./ 40° C. | 12 mo./ 25° C. | 12 mo./ 25° C. | 12 mo./ 25° C. | 12 mo./ /30° C. | 12 mo./ 30° C. | 12 mo./ 30° C. |
| Dv (10) (μm) | 3.97 | 3.85 | 3.95 | 4.02 | 4 | 3.9 | 3.92 | 4 | 3.98 |
| Dv (50) (μm) | 9.65 | 9.4 | 9.62 | 9.79 | 9.73 | 9.51 | 9.51 | 9.77 | 9.69 |
| Dv (90) (μm) | 25 | 24 | 24.9 | 25.4 | 25 | 24 | 24.1 | 25.5 | 24.8 |

In addition, a laboratory batch (Formulation 7) of the celecoxib oral suspension of Example 2 was manufactured and particle size distribution was assessed as described above at time 0 (initial), and out to 30 months. The particle size distribution results were uniform out to 30 months, as shown in Tables 10A-10B.

TABLE 10A

Particle Size Distribution Data (μm) Stability Testing 0 through 30 Months

| | Form. 7 | Ex. 2, Lot A | Ex. 2, Lot B | Ex. 2, Lot C | Ex. 2, Lot A | Ex. 2, Lot B | Ex. 2, Lot C |
|---|---|---|---|---|---|---|---|
| | Age/Temp | | | | | | |
| | Initial | 12 mo/ 25° C. | 12 mo/ 25° C. | 12 mo/ 25° C. | 18 mo/ 25° C. | 18 mo/ 25° C. | 18 mo/ 25° C. |
| Dv (10) | 4.27 | 4.02 | 3.90 | 4.00 | 4.01 | 3.90 | 4.01 |
| Dv (50) | 10.4 | 9.79 | 9.51 | 9.73 | 9.69 | 9.47 | 9.74 |
| Dv (90) | 25.8 | 25.4 | 24.0 | 25.0 | 24.0 | 23.5 | 25.1 |

TABLE 10B

Particle Size Distribution Data (μm) Stability Testing 0 through 30 Months

| | Ex. 2, Lot A | Ex. 2, Lot B | Ex. 2, Lot C | Ex. 2, Lot A | Ex. 2, Lot B | Ex. 2, Lot C |
|---|---|---|---|---|---|---|
| | Age/Temp | | | | | |
| | 24 mo/ 25° C. | 24 mo/ 25° C. | 24 mo/ 25° C. | 30 mo/ 25° C. | 30 mo/ 25° C. | 30 mo/ 25° C. |
| Dv (10) | 4.02 | 3.83 | 3.99 | 3.99 | 3.88 | 3.99 |
| Dv (50) | 9.71 | 9.20 | 9.63 | 9.73 | 9.40 | 9.60 |
| Dv (90) | 24.0 | 20.3 | 23.6 | 26.1 | 24.1 | 24.9 |

The particle size distribution of particles in the oral suspension of Example 2 was compared to that of the comparative oral suspension of Comparative Example 1. As shown in Table 11, the two suspension formulations had similar particle size distributions.

TABLE 11

Comparison of Particle Size Distribution Data (μm)

| Sample Age/ Temperature | Example 2 Lot C 30 mo./ 25° C. | Comparative Example 1 Room Temperature |
|---|---|---|
| Dv (10) | 3.99 | 3.91 |
| Dv (50) | 9.60 | 9.39 |
| Dv (90) | 24.9 | 23.9 |

Example 5—Additional Comparative Studies

Further comparative studies were undertaken with multiple batches prepared per Comparative Example 1 (Table 1) or as described in Example 2 (Table 3) using equipment as appropriate for the batch size.

Comparative Formulation 2 mirrored the oral suspension of Comparative Example 1 (Table 1) and was prepared using a mixer with a sweeping blade and counter rotating paddles. Approximately 95% of the total amount of USP purified water was added to the main vessel large enough to contain the entire batch and equipped with a side sweep blade with counter sweeping paddles. Citric acid was added and mixed to dissolve. Sucralose was added and mixed to dissolve. Sodium citrate was added and mixed to dissolve. Grape flavor was added and mixed to dissolve. To an appropriate-sized side vessel equipped with a propeller blade, propylene glycol was added. Methylparaben was added and mixed to dissolve. Propylparaben was added and mixed to dissolve. Glycerin was added and mixed to disperse. Xanthan gum was added and mixed to disperse. Celecoxib was added and mixed to disperse. The contents of the side vessel were transferred to the main vessel and the side vessel was rinsed with purified water to ensure complete addition and mixed to ensure uniform dispersion. These contents were then transferred into the main tank with mixing. After addition, the batch was recirculated and homogenized for 45 to 60 minutes. The pH was measured to verify the target of pH 5. NaOH or HCl were added if needed to reach the targe pH. USP purified water was added to the target final weight. The finished suspension was mixed to ensure complete and uniform dispersion.

Comparative Formulation 3 was prepared as described above for Comparative Formulation 2, but 0.5% w/v of synthetic magnesium aluminometasilicate was incorporated into the batch via addition to the side vessel.

Comparative Formulation 4 was prepared as described in Example 2, except synthetic magnesium aluminometasilicate was replaced with Veegum® K (0.5% w/v).

Formulation 2 (a composition in accordance with the present disclosure) was prepared as described in Example 2, except the synthetic magnesium aluminometasilicate concentration was reduced to 0.17% w/v (instead of 0.5% w/v).

Formulation 3 (a composition in accordance with the present disclosure) was prepared as described in Example 2, except the xanthan gum concentration was reduced to 0.1% w/v (instead of 0.5% w/v).

Formulation 4 (a composition in accordance with the present disclosure) was prepared as described in Example 2, except the xanthan gum concentration was increased to 0.75% w/v (instead of 0.5% w/v).

Formulation 5 (a composition in accordance with the present disclosure) was prepared as described in Example 2, except the synthetic magnesium aluminometasilicate concentration was increased to 1.0% w/v (instead of 0.5% w/v).

Formulation 6 (a composition in accordance with the present disclosure) was prepared as described in Example 2. A propellor blade was used for mixing, i.e., high shear mixing was not used.

Formulation 7 (a composition in accordance with the present disclosure) was prepared as described in Example 2. A propeller blade was used first for mixing, then the suspension was subsequently mixed with a high-shear blade for 150 additional minutes.

(a) Particle Size Distribution & Microscopy

Formulation 6 and Formulation 7 were subjected to particle size distribution analysis and compared with that of an aged oral suspension prepared as described in Example 2 and stored for 30 months at room temperature (Table 12). The data from Table 11 for Example 2, Lot C is repeated in below to aid comparison.

TABLE 12

| Comparative Particle Size Distribution Data (μm) | | | |
|---|---|---|---|
| Lot | Example 2, Lot C | Formulation 6 | Formulation 7 |
| Dv (10) | 3.99 | 8.31 | 4.27 |
| Dv (50) | 9.60 | 26.6 | 10.4 |
| Dv (90) | 24.9 | 49.3 | 25.8 |

The particle size distribution of Formulation 6 was not similar that of the aged oral suspension of Example 2, likely due to the lack of high shear mixing in the manufacturing process. The particle size distribution of Formulation 7 matched that of the aged oral suspension prepared according to Example 2 and demonstrated that the additional high shear mixing maintained the particle size distribution.

Figure 2:
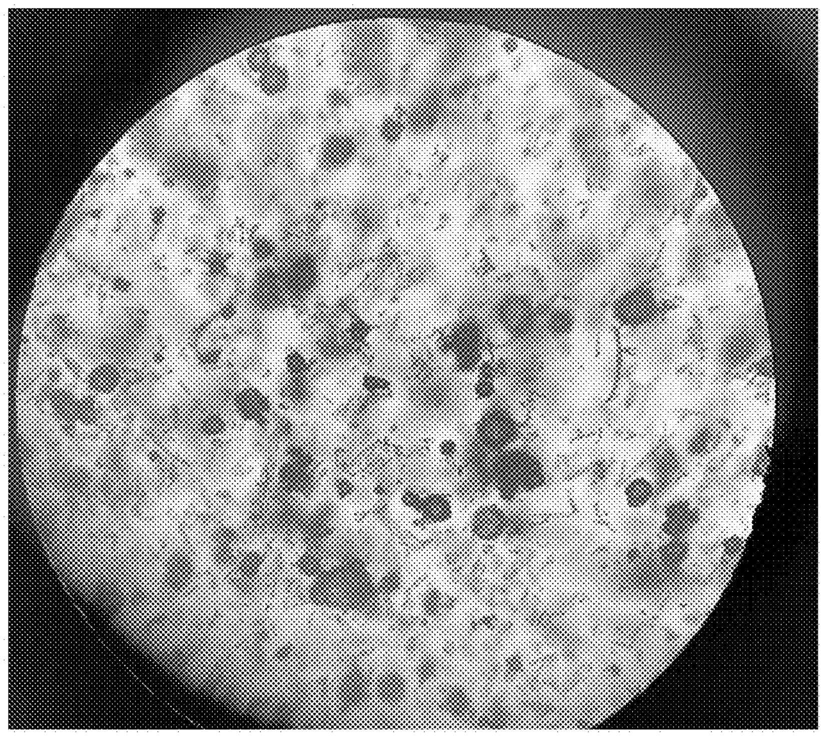
FIG. 2 shows a microscopic image (200×) of a comparative oral celecoxib suspension formulation prepared as described in Example 4.
Figure 3:
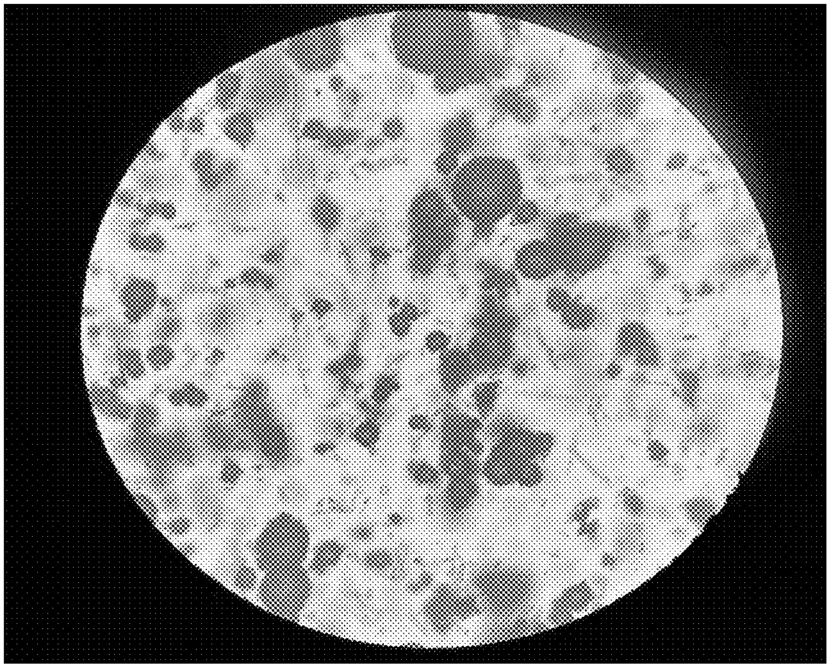
FIG. 3 shows a microscopic image (200×) of Comparative Formulation 3 prepared as described in Example 5.

Microscopy of the oral suspension prepared according to Example 2 is shown in FIG. 1 (200×). Agglomerates were not observed. Microscopy of Comparative Formulation 2 is shown in FIG. 2 (200×). The suspension had multiple agglomerates. Microscopy of Formulation 3 is shown in FIG. 3 (200×). The suspension had multiple agglomerates.

(b) Uniformity Testing

Uniformity testing was performed by removing a sample from different regions of bottles containing celecoxib oral suspensions. The bottles had been stored in an upright orientation at room temperature. Aliquots were pulled from top and bottom portions of the bottle. Each aliquot was used in preparing an individual analytical sample preparation, and each sample preparation was analyzed by HPLC. The HPLC method utilized isocratic conditions at a flow rate of 1.5 mL/min with a Beta Basic Phenyl column (250×4.6 mm, 5 μm) at 60° C. The mobile phase consisted of a mixture of phosphate buffer pH 3.0, methanol and acetonitrile. Celecoxib elution time was approximately 20 minutes. The wavelength of detection was 250 nm.

Products in accordance with the present disclosure (Example 2, Lot B and Formulation 2) and Comparative Formulation 2 were evaluated for percent celecoxib of the label claim (e.g., a finding of 9 mg celecoxib for a product with a label claim of 10 mg celecoxib corresponds to 90% Label Claim celecoxib). The results are shown in Table 13. Comparative Formulation 2, which did not contain synthetic magnesium aluminometasilicate, exhibited significantly greater variability in celecoxib content throughout the bottle from top to bottom as compared to products in accordance with the present disclosure.

TABLE 13

| Top and Bottom Aliquot Data Ranges, % Label Claim Celecoxib | | | |
|---|---|---|---|
| Lot | Comparative Formulation 2 | Formulation 2 | Ex. 2, Lot B |
| Top | 75.0-142.3 | 100.0-102.9 | 103.0-103.2 |
| Bottom | 118.7-158.5 | 99.2-99.3 | 103.3-103.8 |

(c) Unshaken versus Shaken Uniformity Testing

Dispersion uniformity was performed by removing a sample from different regions (top and bottom) of bottles containing celecoxib oral suspensions according to the table below. Bottles had been stored in the upright orientation and measurements were made at 3 months and 6 months of storage at room temperature (25° C.). A bottle containing the oral suspension of Example 2, Lot B, was stored in a horizontal orientation for comparison. Products were evaluated for percent celecoxib of the label claim by HPLC as described above. Each suspension was evaluated after either shaking the bottle vigorously for 30 seconds or without shaking the bottle. The results are shown in Table 14. "Difference" refers to the difference between the top and bottom % LC celecoxib values for a given sample. A smaller difference is indicative of more celecoxib uniformity throughout the different regions of the bottle.

TABLE 14

| % Label Claim Celecoxib in Shaken and Unshaken Bottles | | | | | | | |
|---|---|---|---|---|---|---|---|
| | | 3 months | | | 6 months | | |
| Batch | Shaken or Unshaken | Top % LC Celecoxib | Bottom % LC Celecoxib | Difference | Top % LC Celecoxib | Bottom % LC Celecoxib | Difference |
| Example 2, | Unshaken | 103.0 | 103.3 | 0.3 | 103.2 | 103.8 | 0.5 |
| Lot B | Shaken | N/A | N/A | 0.2 (upright) | N/A | N/A | 0.1 (upright) |

TABLE 14-continued

| % Label Claim Celecoxib in Shaken and Unshaken Bottles | | | | | | | |
|---|---|---|---|---|---|---|---|
| | | 3 months | | | 6 months | | |
| Batch | Shaken or Unshaken | Top % LC Celecoxib | Bottom % LC Celecoxib | Difference | Top % LC Celecoxib | Bottom % LC Celecoxib | Difference |
| | | | | 0.7 (horizontal) | | | 1.8 (horizontal) |
| Comparative | Unshaken | 102.6 | 118.7 | 16.1 | 75 | 158.5 | 83.5 |
| Formulation 2 | Shaken | 99.6 | 100.4 | 0.8 | 101.1 | 101.4 | 0.3 |
| Formulation 2 | Unshaken | 102.9 | 99.3 | 3.6 | 100 | 99.2 | 0.8 |
| | Shaken | 100.1 | 100 | 0.1 | 100.5 | 101 | 0.5 |

Comparative Formulation 2, which did not contain synthetic magnesium aluminometasilicate, exhibited greater variability in celecoxib content throughout the bottle as compared to products in accordance with the present disclosure (Example 2, Lot B and Formulation 2). This was true regardless of whether Comparative Formulation 2 was shaken or not prior to evaluation, although shaking redispersed the suspension and provided better uniformity. The unshaken bottle containing Comparative Formulation 2 exhibited substantial settling over time, resulting in a difference of 83.5% LC celecoxib content between the top and bottom by 6 months. In contrast, products in accordance with the present disclosure (Example 2, Lot B and Formulation 2) exhibited minimal variability in % LC celecoxib content at 3 and 6 months regardless of storage orientation. Additionally, the products in accordance with the present disclosure did not require shaking; unshaken bottles exhibited satisfactory celecoxib uniformity throughout the bottle even after six months of storage.

(d) Centrifugation Study

To further investigate the variability observed above, a centrifugation study was performed to simulate finished product settling over time. The bottle was shaken for 15 seconds to redisperse any settled material. 15 mL of suspension was placed into a centrifuge tube. The sample was centrifuged for 5 minutes at approximately 4000 rpm. 5 mL from the supernatant was used in preparing an individual analytical sample preparation, and each sample preparation was analyzed. A second set of samples was prepared in the same manner, with a centrifugation time of 30 minutes. The results are shown in Table 15.

TABLE 15

| Uniformity - Centrifuge Data | | |
|---|---|---|
| Batch | Supernatant % Label Claim Celecoxib 5 min Centrifuging | Supernatant % Label Claim Celecoxib 30 min Centrifuging |
| Comparative Formulation 2 | 17.6 | 5.3 |
| Comparative Formulation 3 | 10.0 | 2.7 |
| Example 2, Lot C | 98.7 | 59.1 |
| Formulation 2 | 47.4 | 24.3 |

TABLE 15-continued

| Uniformity - Centrifuge Data | | |
|---|---|---|
| Batch | Supernatant % Label Claim Celecoxib 5 min Centrifuging | Supernatant % Label Claim Celecoxib 30 min Centrifuging |
| Formulation 6 | 66.1 | 30.8 |
| Formulation 7 | 102.2 | 69.7 |

There was a clear difference, visually and analytically, between formulations based on Comparative Example 1 (Table 1) and those based on the new products and processes described herein (e.g., Example 2, Table 3). Comparative Formulation 2 showed separation at 5 min centrifuging, with less than 20% celecoxib remaining in suspension, and 5% remaining after 30 minutes. Mere addition of synthetic magnesium aluminometasilicate to Comparative Formulation 2 (resulting in Comparative Formulation 3) did not improve the results. The products in accordance with the present disclosure prepared with high shear mixing (Formulation 7 and Example 2, Lot C) did not show separation at 5 min centrifuging and ~60-70% celecoxib remained in the suspension after 30 min centrifuging.

(e) Redispersibility Testing

Redispersibility testing was performed on the batches of a product in accordance with the present disclosure (Example 2, Lots A-C) following storage in the horizontal and upright position for 24 months at 25° C. and 40% relative humidity (RH). For each test, the bottle was shaken vigorously for 30 seconds immediately prior to sampling. A sample (20 grams) was pulled from the top portion of the bottle and accurately weighed directly into a 200 mL volumetric flask. A sample (20 grams) was pulled from the bottom portion of the bottle and accurately weighed directly into a 200 mL volumetric flask. For both flasks, the sample was dissolved and diluted to volume with methanol. The contents were mixed well and sonicated for 10 minutes. An aliquot of the analytical sample preparation was filtered through a 0.45 μm PTFE syringe filter, with the first 2-3 mL of filtrate discarded and the next portion transferred into an HPLC vial. The results are shown in Table 16.

TABLE 16

| 24 Months Redispersibility Data | | | | | | |
|---|---|---|---|---|---|---|
| | Lot A | | Lot B | | Lot C | |
| Description | Upright | Horizontal | Upright | Horizontal | Upright | Horizontal |
| % Label Claim Celecoxib, Top | 100.9 | 101.5 | 101.9 | 101.1 | 100.8 | 100.4 |
| % Label Claim Celecoxib, Bottom | 101.3 | 102.6 | 99.6 | 101.5 | 104.1 | 101.2 |
| % Difference | 0.4 | 1.1 | 2.4 | 0.4 | 3.3 | 0.9 |

A minimal difference in product uniformity was observed for the product in accordance with the present disclosure after 24 months of storage regardless of whether the bottle was stored in the horizontal or upright position.

(f) Dissolution Testing

Dissolution testing of lab-scale batches having different concentrations of xanthan gum and synthetic magnesium aluminometasilicate were compared to the dissolution profile of a product in accordance with the present disclosure (Example 2, Lot C). The following dissolution test method was used:

Media: 0.04M Sodium Phosphate Tribasic, pH adjusted to 11.1 with $H_3PO_4$, with an SDS concentration of 0.5%.

Media Volume: 100 mL

Paddle Speed: 75 rpm Media Temperature: 37° C.

Dispensing: Sampled 5 mL of dissolution media from each vessel and reserve. Dispensed 20 mL of Celecoxib Oral Suspension, 10 mg/mL, into a dosing cup. Poured the cup contents into the vessel in approximately 10 seconds. Added the 5 mL of reserved media to the cup and mixed gently. Poured the rinse solution into the vessel. The time for the full addition was approximately 20-30 seconds.

Sampling: For each vessel, sampled 5 mL of media through a filtered cannula into a syringe. Detached the cannula, placed a syringe filter onto the syringe. Filtered through syringe filter into HPLC vial, discarding the first 2 mL.

Sampling points: 5, 10, 15, 20, 30, 45, 60, and 90 minutes after sample addition.

HPLC Column: Phenomenex, Gemini C6 Phenyl, 150 mm×4.6 mm×3 μm.

Full dissolution data is provided in Table 17.

TABLE 17

| Lab-Scale Batches, % celecoxib dissolved | | | | | | |
|---|---|---|---|---|---|---|
| Time Point (min) | Example 2, Lot C | Comparative Formulation 2 | Formulation 2 | Formulation 3 | Formulation 4 | Formulation 5 |
| 5 | 14.61 | 92.58 | 16.75 | 81.89 | 5.89 | 12.37 |
| 10 | 29.63 | 96.63 | 36.05 | 86.80 | 9.41 | 37.18 |
| 15 | 50.90 | 98.48 | 52.24 | 90.04 | 15.94 | 53.96 |
| 20 | 69.96 | 99.23 | 72.18 | 93.13 | 22.36 | 71.51 |
| 30 | 90.85 | 99.85 | 89.00 | 96.23 | 34.67 | 83.57 |
| 45 | 101.20 | 100.00 | 99.18 | 97.57 | 60.24 | 97.21 |
| 60 | 101.96 | 99.87 | 98.63 | 98.88 | 68.57 | 95.25 |
| 90 | 102.47 | 99.62 | 100.18 | 99.48 | 84.41 | 95.73 |

A similarity factor (f2) value greater than or equal to 50 indicates a sufficiently similar dissolution profile. Table 18 shows the similarity factors for the various formulations as well as the compositional differences from the test formulations compared to the oral suspension of Example 2 (0.5% w/v xanthan gum and 0.5% w/v synthetic magnesium aluminometasilicate).

TABLE 18

| Lab-Scale Batches, f2 values versus Oral Suspension of Example 2 | | |
|---|---|---|
| Formulation | Composition difference from oral suspension of Example 2 | f2 |
| Comparative Formulation 2 | 0% synthetic magnesium aluminometasilicate, 0.25% xanthan gum | Not applicable |
| Formulation 2 | 0.17% synthetic magnesium aluminometasilicate | 71 |
| Formulation 3 | 0.1% xanthan gum | 9 |
| Formulation 4 | 0.75% xanthan gum | 25 |
| Formulation 5 | 1% synthetic magnesium aluminometasilicate | 68 |

Formulation 2 and Formulation 5 had similar celecoxib dissolution characteristics to the oral suspension of Example 2. Comparative Formulation 2, Formulation 3, and Formulation 4 demonstrated celecoxib dissolution profiles which were significantly different from the oral suspension of Example 2. The f2 approach is not suitable for drug products that dissolve very rapidly (i.e., greater than or equal to 85 percent of the drug product is dissolved in 15 minutes or less), such as Comparative Formulation 2.

Figure 4:
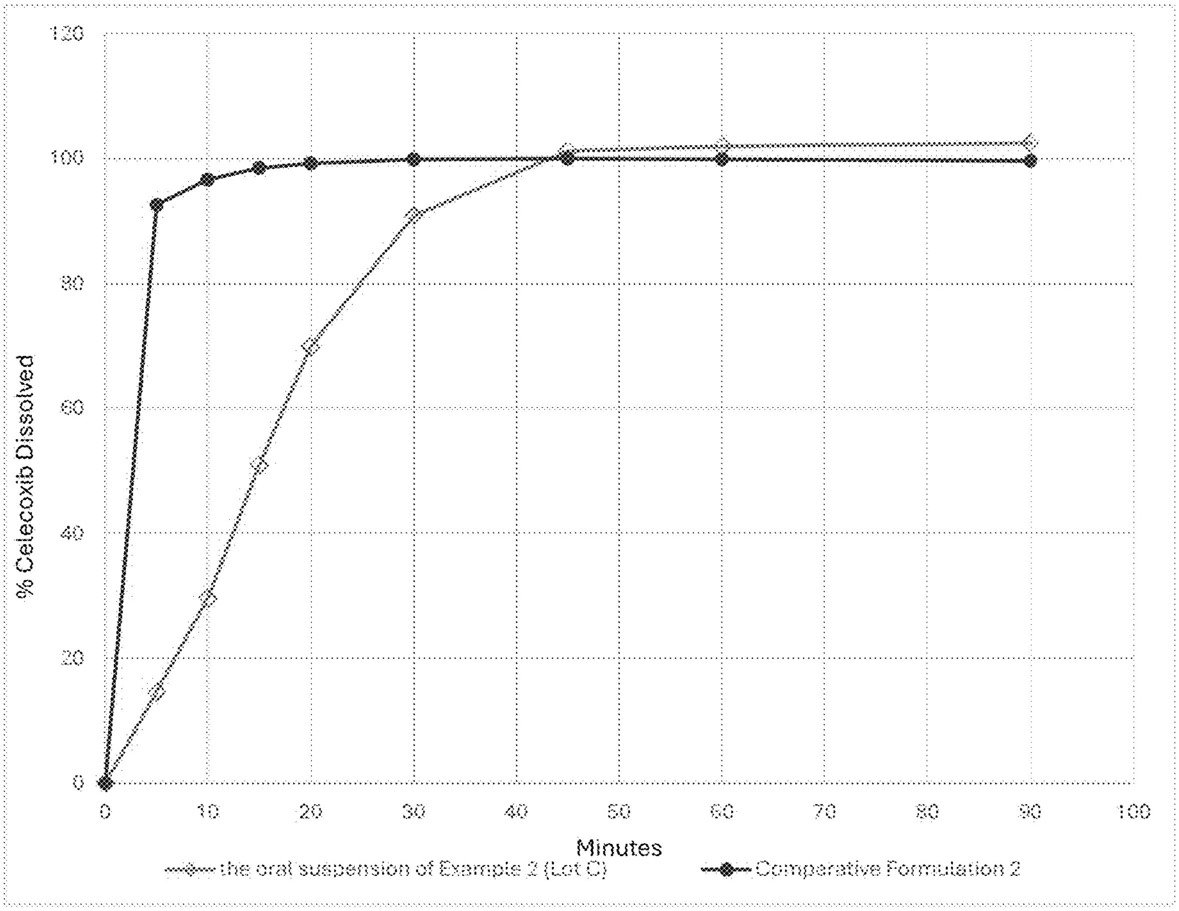
FIG. 4 shows the mean dissolution profiles of Comparative Formulation 2 and a registration batch of the oral celecoxib suspension of Example 2.

FIG. 4 shows the mean celecoxib dissolution profiles of Comparative Formulation 2 (which mimics the comparative oral suspension of Comparative Example 1) and a product in accordance with the present disclosure (the oral suspension of Example 2, Lot C). The product in accordance with the present disclosure had a markedly slower dissolution profile.

Figure 5:
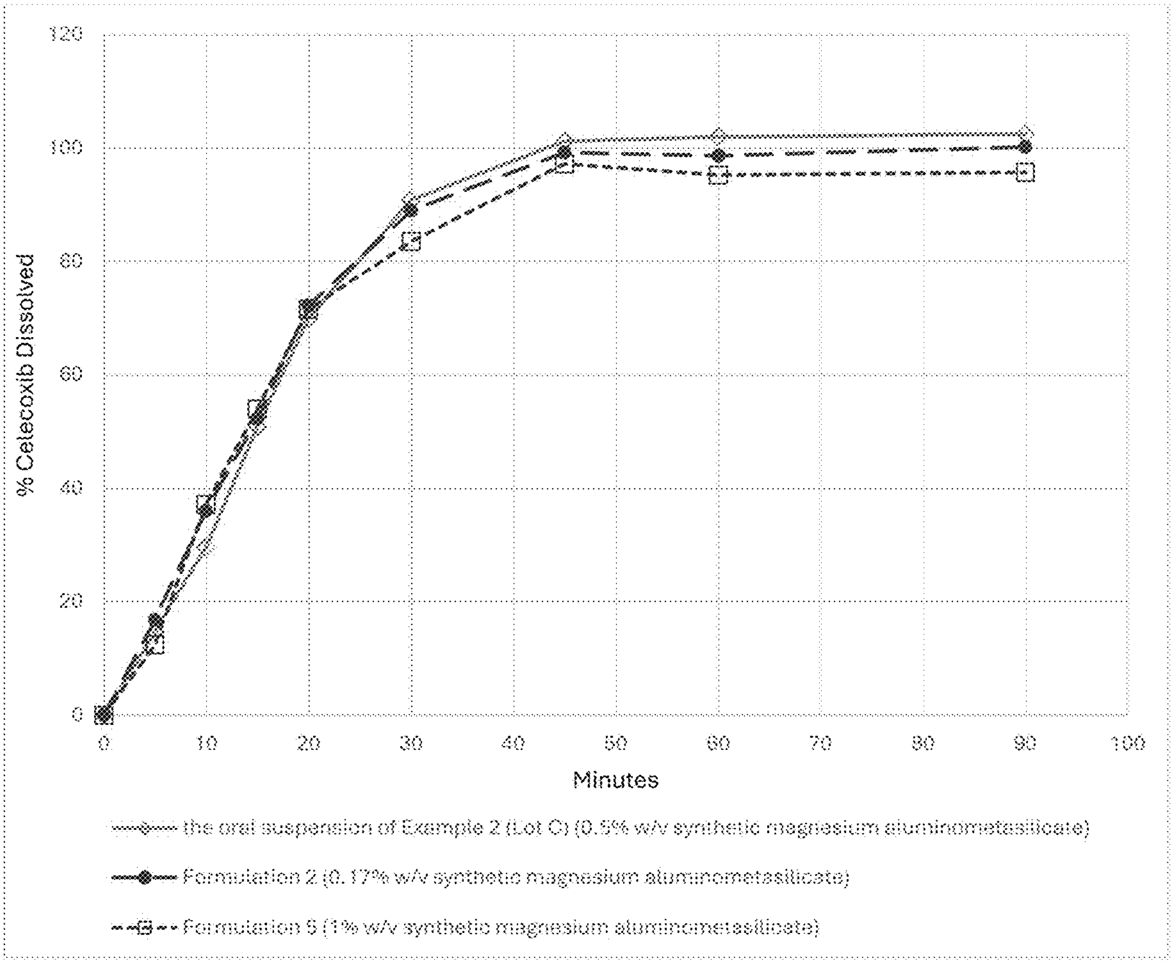
FIG. 5 shows the mean dissolution profiles of three celecoxib formulations in accordance with the present disclosure with differing amounts of synthetic magnesium aluminometasilicate. From top to bottom: the oral celecoxib suspension of Example 2 (Lot C) (0.5% w/v synthetic magnesium aluminometasilicate), Formulation 2 (0.17% w/v synthetic magnesium aluminometasilicate), and Formulation 5 (1% w/v synthetic magnesium aluminometasilicate).
Figure 6:
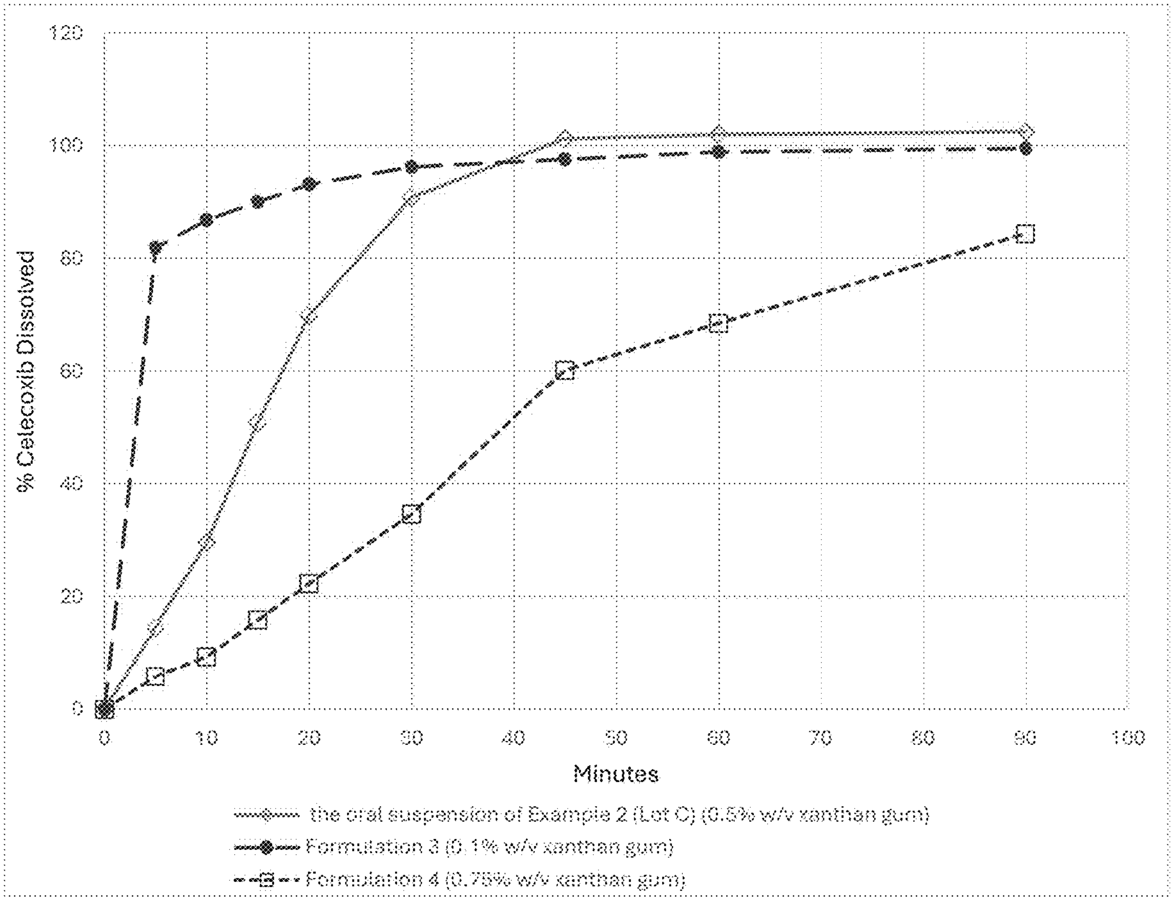
FIG. 6 shows the mean dissolution profiles of three celecoxib formulations in accordance with the present disclosure with differing amounts of xanthan gum. From top to bottom: the oral suspension of Example 2 (Lot C) (0.5% w/v xanthan gum), Formulation 3 (0.1% w/v xanthan gum), and Formulation 4 (0.75% w/v xanthan gum).

FIG. 5 shows that varying the synthetic magnesium aluminometasilicate content in a product in accordance with the present disclosure from 0.17% to 1% had minimal effect on the rate of celecoxib dissolution. FIG. 6 shows that the celecoxib dissolution rate is impacted by xanthan gum concentration, with increasing xanthan gum concentrations demonstrating slower dissolution.

(g) pH Stability Testing

Multiple experiments were performed with formulations having 1% w/v synthetic magnesium aluminometasilicate, in an attempt to prepare pH-stable formulations. Parameters that were varied included the ratios and strengths of citric acid buffer and a step of hydrating the synthetic magnesium aluminometasilicate prior to use (e.g., in water or aqueous buffer and sucralose). In all cases, the formulation demonstrated pH instability. Formulations prepared without synthetic magnesium aluminometasilicate were pH stable. Formulations prepared with purified (natural) magnesium aluminum silicate material (e.g., Veegum® HS and Veegum® HV) were pH stable, but the formulation striated and quickly became non-uniform. A summary of the pH studies is provided in Table 19.

TABLE 19

Summary of pH Instability

| Formulation | Synthetic magnesium aluminometasilicate (% w/v) | pH Change | | Time (days) | Showed pH Stability |
|---|---|---|---|---|---|
| Comparative Formulation 4 | 1.0 | 4.36 | 5.90 | 1 | No |
| Comparative Formulation 5 | 0.0 | 4.78 | 4.79 | 3 | Yes |
| Comparative Formulation 6 | 1.0 | 5.31 | 6.61 | 1 | No |
| Comparative Formulation 6 + hydration | 1.0 | 5.23 | 6.22 | 0.3 | No |
| Comparative Formulation 6 + hydration | 1.0 | 6.22 | 6.90 | 1 | No |
| Comparative Formulation 7 | 1.0 | 5.02 | 5.07 | 1 | Yes |
| Comparative Formulation 8 | 1.0 | 5.12 | 5.20 | 1 | Yes |
| Formulation 8 | 0.5 | 5.11 | 5.33 | 180 | Yes |
| Formulation 2 | 0.17 | 5.01 | 5.01 | 180 | Yes |

Comparative Formulation 7 had the same composition as Comparative Formulation 6, except Veegum® HS (Vanderbilt Minerals, LLC), a purified bentonite, magnesium aluminum silicate, was used in place of synthetic magnesium aluminometasilicate. Comparative Formulation 7 showed pH stability, but was striated and visually non-uniform after sitting overnight.

Comparative Formulation 8 had the same composition as Comparative Formulation 7, but Veegum® HV (Vanderbilt Minerals, LLC), a purified smectite clay, magnesium aluminum silicate, was used in place of magnesium aluminometasilicate. Comparative Formulation 8 exhibited reasonably stable pH, but after sitting overnight the batch was striated and visually appeared non-uniform.

Formulation 8, a product in accordance with the present disclosure, was prepared with 0.5% w/v synthetic magnesium aluminometasilicate (Table 20).

TABLE 20

Formulation 8 (0.5% w/v synthetic magnesium aluminometasilicate)

| Material | % W/V | Target Weight (g) |
|---|---|---|
| Celecoxib | 1.00 | 30.00 |
| Xanthan Gum | 0.50 | 15.00 |
| Citric Acid Anhydrous | 0.70 | 21.00 |
| Sodium Citrate Dihydrate | 1.10 | 33.00 |
| Grape Flavor | 0.30 | 9.00 |
| Glycerin | 15.00 | 450.00 |
| Sucralose | 0.10 | 3.00 |
| Synthetic magnesium aluminometasilicate | 0.50 | 15.00 |
| Methylparaben Sodium | 0.172 | 5.16 |
| Propylparaben Sodium | 0.056 | 1.68 |
| DI Water | 85.572 (QS) | 2,567.16 (QS) |
| Total | 105.00* | 3,150.00* |

The initial pH of the completed batch was 5.11. When stored at 25° C., the pH at one month was 5.28 and the pH at 6 months was 5.33. When stored at 40° C., the pH at 1 month was 5.29 and the pH at 6 months was 5.34. Thus, this formulation exhibited acceptable pH stability.

Formulation 2, a product in accordance with the present disclosure, had a synthetic magnesium aluminometasilicate concentration of 0.17% w/v (see Table 3). The pH was 5.01 initially. When stored at 40° C., the pH was 4.92 at one month, 4.93 at 2 months, 4.93 at 3 months, and 5.01 at 6 months. Thus, this formulation exhibited acceptable pH stability.

In summary, the oral suspension of Comparative Example 1 exhibited agglomeration, poor uniformity, and poor redispersibility. Addition of 1% w/v synthetic magnesium aluminometasilicate and a different method of manufacture mitigated some of these aspects but led to pH instability. In contrast, products in accordance with the present disclosure do not exhibit agglomeration or significant pH changes over time. Additionally, products in accordance with the present disclosure exhibit superior uniformity and redispersibility properties as well as a slower celecoxib dissolution profile, as compared to other formulations including Comparative Example 1.

Example 6—Acid Neutralizing Capacity

The acid neutralizing capacity of the oral suspension of Comparative Example 1 (Table 1), a product in accordance with the present disclosure (Example 2, Table 3), a CELEBREX® capsule (200 mg), and an antacid tablet (1,000 mg calcium carbonate) were evaluated following the guidance in USP Monograph <301> Acid-Neutralizing Capacity:

Transfer an accurately weighed quantity of the uniform mixture, equivalent to the minimum labeled dosage, to a 250-mL beaker, add water to make a total volume of about 70 mL, and mix on the Magnetic stirrer for 1 minute.

Pipet 30.0 mL of 1.0 N hydrochloric acid VS into the Test preparation while continuing to stir with the Magnetic stirrer. Stir for 15 minutes, accurately timed, after the addition of the acid.

Utilizing a standardized pH meter, begin to titrate immediately, and in a period not to exceed an additional 5 minutes, titrate the excess hydrochloric acid with 0.5 N sodium hydroxide VS to attain a stable (for 10 to 15 seconds) pH of 3.5.

The number of mEq of acid consumed is calculated via the formula:

$$\text{Total } mEq = (30 \times N_{HCl}) - (V_{NaOH} \times N_{NaOH})$$

$N_{HCl}$=Normality of Hydrochloric Acid VS $V_{NaOH}$=Volume of Sodium Hydroxide VS utilized for titration $N_{NaOH}$=Normality of Sodium Hydroxide VS The results are shown in Table 21:

TABLE 21

Summary of acid-neutralizing capacity (n = 3)

| | | |
|---|---|---|
| Comparative Example 1 (Table 1) | Mean = 1.82<br>Std Dev = 0.05<br>% RSD = 2.7 | mEq per 200 mg dose |
| Example 2 (Table 3) | Mean = 2.59<br>Std Dev = 0.11<br>% RSD = 4.2 | mEq per 200 mg dose |
| CELEBREX ® Capsule | Mean = 0.64<br>Std Dev = 0.03<br>% RSD = 4.7 | mEq per 200 mg dose |
| Antacid Tablet | Mean = 21.27<br>Std Dev = 0.11<br>%R SD = 0.5 | mEq per 1000 mg tablet |

A discernable difference in acid neutralizing capabilities between the oral suspension of Comparative Example 1 and the product in accordance with the present disclosure was observed. The acid neutralizing capacity of the product in accordance with the present disclosure was 2.59 mEq per dose, whereas the acid neutralizing capacity of the oral suspension of Comparative Example 1 was 1.82 mEq per dose.

A more profound distinction in acid neutralizing capacity was observed between the product in accordance with the present disclosure and CELEBREX® capsules, as the acid neutralizing capacity of the product in accordance with the present disclosure was almost four times that of the CELEBREX® capsule.

The acid neutralizing capacity of the product in accordance with the present disclosure was compared to the acid neutralizing capacity of an antacid (calcium carbonate) tablet containing 1,000 mg of the antacid. The product in accordance with the present disclosure demonstrated a value of 2.59 mEq, about 12% of 21.27 mEq for the 1000 mg Antacid tablet.

While the acid neutralizing capacity of the product in accordance with the present disclosure was not sufficient for it to be classified as an antacid, the higher acid neutralizing capacity versus CELEBREX® capsules will result in diminished stomach discomfort (e.g., gastric upset and indigestion) typically associated with continued, daily usage of NSAIDs including CELEBREX® capsules.

8. Equivalents

While the subject matter of the present disclosure has been particularly shown and described with reference to specific embodiments and various alternate embodiments, it will be understood by persons skilled in the relevant art that various changes in form and details can be made therein without departing from the spirit and scope of the provided disclosure.

What is claimed is:

1. A liquid pharmaceutical composition comprising:
from 0.1 mg/mL to 100 mg/mL celecoxib,
suspending agents comprising xanthan gum and from 0.1% w/v to 0.75% w/v of a synthetic magnesium aluminometasilicate, wherein the xanthan gum and synthetic magnesium aluminometasilicate are present in a weight ratio of 1:1, and
a liquid carrier,
wherein the composition is in the form of a suspension.

2. The liquid pharmaceutical composition of claim 1, wherein the celecoxib is present at a concentration from 1 mg/mL to 20 mg/mL.

3. The liquid pharmaceutical composition of claim 1, wherein the celecoxib is present at a concentration from 5 mg/mL to 15 mg/mL.

4. The liquid pharmaceutical composition of claim 1, wherein the celecoxib is present at a concentration of 10 mg/mL.

5. The liquid pharmaceutical composition of claim 1, wherein the celecoxib is celecoxib polymorphic Form III.

6. The liquid pharmaceutical composition of claim 1, wherein the composition comprises celecoxib-containing particles having a particle size distribution with a D10 of from 1 to 5 μm, a D50 from 8 to 12 μm, and a D90 from 20 to 26 μm.

7. The liquid pharmaceutical composition of claim 1, wherein the composition comprises celecoxib-containing particles having a particle size distribution with a D10 of not less than (NLT) 1 μm, a D50 from 5 μm to 12.5 μm, and a D90 of not more than (NMT) 30 μm.

8. The liquid pharmaceutical composition of claim 1, wherein the suspending agents consist essentially of a mixture of xanthan gum and from 0.1% w/v to 0.75% w/v of a synthetic magnesium aluminometasilicate.

9. The liquid pharmaceutical composition of claim 1, wherein the xanthan gum is present in an amount from 0.25% w/v to 0.75% w/v of the composition.

10. The liquid pharmaceutical composition of claim 1, wherein the synthetic magnesium aluminometasilicate is present in an amount from 0.2% w/v to 0.6% w/v of the composition.

11. The liquid pharmaceutical composition of claim 1, wherein the xanthan gum is present in an amount from 0.25% w/v to 0.6% w/v of the composition and the synthetic magnesium aluminometasilicate is present in an amount from 0.25% w/v to 0.6% w/v of the composition.

12. The liquid pharmaceutical composition of claim 1, wherein the synthetic magnesium aluminometasilicate exhibits one or more or all of the following properties: (a) the synthetic magnesium aluminometasilicate is in amorphous form, (b) the synthetic magnesium aluminometasilicate has a loose bulk density from 0.06 to 0.11 g/mL, (c) the synthetic magnesium aluminometasilicate has a tapped bulk density from 0.1 to 0.17 g/mL, and (d) the synthetic magnesium aluminometasilicate has an average particle size of 3.1 μm.

13. The liquid pharmaceutical composition of claim 1, further comprising one or more pharmaceutically acceptable excipients selected from preservatives, sweetening agents, buffering agents, coloring agents, flavoring agents, and pH modifiers.

14. The liquid pharmaceutical composition of claim 1, wherein the liquid carrier comprises water and a wetting agent.

15. The liquid pharmaceutical composition of claim 14, wherein the wetting agent is selected from glycols, glycol ether, glycerin, polyoxyethylene alcohols, polyoxyethylene fatty acid esters, and combinations thereof.

16. The liquid pharmaceutical composition of claim 1 comprising:
- from 1 mg/mL to 20 mg/mL celecoxib;
- suspending agents comprising from 0.25% w/v to 0.6% w/v xanthan gum and from 0.25% w/v to 0.6% w/v of a synthetic magnesium aluminometasilicate;
- from 0.01% w/v to 1% w/v of a preservative;
- from 0.1% w/v to 2% w/v of a buffering agent;
- from 0.01% w/v to 1% w/v of a sweetening agent; and
- a liquid carrier comprising from 80% w/v to 95% w/v water and from 1% w/v to 20% w/v of a wetting agent.

17. The liquid pharmaceutical composition of claim 1 comprising:
- 10 mg/mL celecoxib;
- suspending agents comprising 0.5% w/v xanthan gum and 0.5% w/v of a synthetic magnesium aluminometasilicate;
- from 0.05% w/v to 0.5% w/v of a preservative;
- from 0.1% w/v to 2% w/v of a buffering agent;
- from 0.05% w/v to 0.5% w/v of a sweetening agent; and
- a liquid carrier comprising from 80% w/v to 90% w/v water and from 10% w/v to 20% w/v of a wetting agent.

18. The liquid pharmaceutical composition of claim 17, wherein:
- the preservative comprises methyl paraben and propyl paraben,
- the buffering agent comprises citric acid and sodium citrate dihydrate,
- the sweetening agent comprises sucralose, and
- the liquid carrier comprises water and glycerin.

19. The liquid pharmaceutical composition of claim 1, wherein the composition has a pH from 3 to 9.

20. The liquid pharmaceutical composition of claim 1, wherein the composition has a pH above 5.2.

21. The liquid pharmaceutical composition of claim 1, wherein the composition exhibits one or more or all of the following properties:
- (a) the pH of the composition does not change by more than 0.5 following storage for one month at 25° C.;
- (b) the composition, when in the form of a suspension, exhibits one or both of (i) a uniformity difference in celecoxib content between the top of the composition and the bottom of the composition of less than 5% following storage in a closed bottle at 25° C. in an upright orientation for six months and (ii) a uniformity difference in celecoxib content between the top of the composition and the bottom of the composition of less than 5% following storage in a closed bottle at 40° C. in an upright orientation for six months, wherein the composition is shaken for 30 seconds prior to measuring celecoxib content;
- (c) the composition, when subjected to dissolution testing at 37° C. at a paddle speed of 75 rpm in 1000 ml of dissolution media consisting of 0.04M sodium phosphate tribasic, pH adjusted to 11.1 with $H_3PO_4$, with a sodium dodecyl sulfate (SDS) concentration of 0.5%, exhibits a celecoxib release profile characterized by:
  - (i) from 5% to 45% celecoxib release in 5 minutes,
  - (ii) from 15% to 50% celecoxib release in 10 minutes,
  - (iii) from 30% to 75% celecoxib release in 15 minutes,
  - (iv) from 55% to 85% celecoxib release in 20 minutes, and
  - (v) greater than 80% celecoxib release in 30 minutes
- (d) oral administration to a subject of a dose of the liquid pharmaceutical composition in the form of a suspension comprising from 50 mg to 200 mg celecoxib is bioequivalent to oral administration of a capsule formulation containing the same amount of celecoxib, wherein the liquid pharmaceutical composition in the form of a suspension comprises 1% w/v celecoxib, 0.5% w/v xanthan gum, 0.5% w/v synthetic magnesium aluminometasilicate, 0.7% w/v citric acid anhydrous, 1.1% w/v sodium citrate dihydrate, 0.15% w/v methylparaben, 0.05% w/v propylparaben, 0.1% w/v sucralose, 15.0% w/v glycerin, and water, and wherein the capsule formulation comprises celecoxib, A croscarmellose sodium, edible inks, gelatin, lactose monohydrate, magnesium stearate, povidone, and sodium lauryl sulfate;
- (e) the composition has an acid neutralizing capacity from 2 mEq to 5 mEq per 200 mg dose.

22. The liquid pharmaceutical composition of claim 1, wherein the composition does not include one or more or all of sodium lauryl sulfate, propylene glycol, and purified natural magnesium aluminum silicate.

* * * * *